(12) United States Patent
Rousseau

(10) Patent No.: US 9,974,683 B2
(45) Date of Patent: May 22, 2018

(54) FLEXIBLE IMPLANTS HAVING INTERNAL VOLUME SHIFTING CAPABILITIES FOR TREATING OBSTRUCTIVE SLEEP APNEA

(75) Inventor: Robert A. Rousseau, Ottsville, PA (US)

(73) Assignee: Ethicon, Inc., Somerville, NJ (US)

(*) Notice: Subject to any disclaimer, the term of this patent is extended or adjusted under 35 U.S.C. 154(b) by 218 days.

(21) Appl. No.: 12/609,424

(22) Filed: Oct. 30, 2009

(65) Prior Publication Data
US 2011/0100378 A1    May 5, 2011

(51) Int. Cl.
*A61F 5/56*    (2006.01)

(52) U.S. Cl.
CPC ................... *A61F 5/566* (2013.01)

(58) Field of Classification Search
CPC ...... A61F 5/566; A61F 5/56; A61F 2002/523; A61F 5/08; A61F 2/18; A61F 2002/183; A61F 2/186; A61F 2/441; A61F 2002/444; A61F 2002/30586; A61M 25/10; A61M 25/1002; A61M 25/1011; A61M 2025/1013; A61M 2025/1015; A61M 29/02; A61M 2025/0035; A61M 2025/004; A61M 25/0026; A61M 2025/1054; A61B 2017/248; A61B 2018/00333; A61B 17/7097; B29D 22/02
USPC ............... 128/848, 846, 845, 885, 886, 887; 602/902; 600/237, 207, 206, 201; 606/192; 623/7, 8, 10, 17.12
See application file for complete search history.

(56) References Cited

U.S. PATENT DOCUMENTS

| 3,123,077 A | 3/1964 | Alcamo |
| 3,378,010 A | 4/1968 | Codling et al. |

(Continued)

FOREIGN PATENT DOCUMENTS

| CN | 2465680 | 12/2001 |
| CN | 201029957 | 3/2008 |

(Continued)

OTHER PUBLICATIONS

Harries et al., "The Surgical treatment of snoring", Journal of Laryngology and Otology, pp. 1105-1106 (1996).
(Continued)

*Primary Examiner* — Victoria J Hicks
(74) *Attorney, Agent, or Firm* — Doherty IP Law Group LLC

(57) ABSTRACT

An implant for treating obstructive sleep apnea includes a first chamber containing an incompressible fluid, a second chamber containing a compressible fluid, and a flexible diaphragm separating the first and second chambers. The incompressible fluid is in communication with the compressible fluid via the flexible diaphragm. The first chamber has a first volume that remains constant in response to an external force applied upon the implant and the second chamber has a second volume that is changeable when the external force is applied upon the implant. The flexible diaphragm is extendible into the second chamber for reducing the second volume of the second chamber and compressing the compressible fluid within the second chamber. The compressible fluid within the second chamber provides less resistance to flexing during initial flexing of the implant and more resistance to flexing during further flexing of the implant.

21 Claims, 14 Drawing Sheets

(56) References Cited

U.S. PATENT DOCUMENTS

| | | | |
|---|---|---|---|
| 4,069,825 A | 1/1978 | Akiyama | |
| 4,290,763 A | 9/1981 | Hurst | |
| 4,523,584 A | 6/1985 | Yachia et al. | |
| 4,557,264 A | 12/1985 | Hinsch | |
| 4,790,848 A * | 12/1988 | Cronin | A61F 2/12 623/8 |
| 4,839,215 A | 6/1989 | Starling et al. | |
| 4,881,939 A | 11/1989 | Newman | |
| 4,950,285 A | 8/1990 | Wilk | |
| 5,053,047 A | 10/1991 | Yoon | |
| 5,067,485 A | 11/1991 | Cowen | |
| 5,123,913 A | 6/1992 | Wilk et al. | |
| 5,192,271 A | 3/1993 | Kalb et al. | |
| 5,192,274 A | 3/1993 | Bierman | |
| 5,269,783 A | 12/1993 | Sander | |
| 5,284,161 A | 2/1994 | Karell | |
| 5,311,028 A | 5/1994 | Glavish | |
| 5,393,984 A | 2/1995 | Glavish | |
| 5,483,077 A | 1/1996 | Glavish | |
| 5,484,444 A | 1/1996 | Braunschweiler et al. | |
| 5,609,559 A | 3/1997 | Weitzner | |
| 5,683,417 A | 11/1997 | Cooper | |
| 5,704,895 A | 6/1998 | Scott et al. | |
| 5,792,067 A | 8/1998 | Karell | |
| 5,843,077 A | 12/1998 | Edwards | |
| 5,931,855 A | 8/1999 | Buncke | |
| 6,161,541 A | 12/2000 | Woodson | |
| 6,190,401 B1 | 2/2001 | Green et al. | |
| 6,241,747 B1 | 6/2001 | Ruff | |
| 6,250,307 B1 | 6/2001 | Conrad et al. | |
| 6,348,156 B1 | 2/2002 | Vishnoi et al. | |
| 6,408,851 B1 | 6/2002 | Karell | |
| 6,431,174 B1 | 8/2002 | Knudson et al. | |
| 6,432,437 B1 | 8/2002 | Hubbard | |
| 6,457,472 B1 | 10/2002 | Schwartz et al. | |
| 6,513,530 B2 | 2/2003 | Knudson et al. | |
| 6,523,542 B2 | 2/2003 | Knudson et al. | |
| 6,578,580 B2 | 6/2003 | Conrad et al. | |
| 6,589,549 B2 | 7/2003 | Shih et al. | |
| 6,599,310 B2 | 7/2003 | Leung et al. | |
| 6,627,600 B2 | 9/2003 | Boutignon | |
| 6,634,362 B2 | 10/2003 | Conrad et al. | |
| 6,638,284 B1 | 10/2003 | Rousseau et al. | |
| 6,716,251 B1 | 4/2004 | Asius et al. | |
| 6,742,524 B2 | 6/2004 | Knudson et al. | |
| 6,755,868 B2 | 6/2004 | Rousseau | |
| 6,800,082 B2 | 10/2004 | Rousseau | |
| 6,899,105 B2 | 5/2005 | Krueger et al. | |
| 6,955,172 B2 | 10/2005 | Nelson et al. | |
| 6,981,944 B2 | 1/2006 | Jamiolkowski et al. | |
| 7,017,582 B2 | 3/2006 | Metzger et al. | |
| 7,056,331 B2 | 6/2006 | Kaplan et al. | |
| 7,135,189 B2 | 11/2006 | Knapp | |
| 7,146,981 B2 | 12/2006 | Knudson et al. | |
| 7,166,570 B2 | 1/2007 | Hunter et al. | |
| 7,213,599 B2 | 5/2007 | Conrad et al. | |
| 7,237,554 B2 | 7/2007 | Conrad et al. | |
| 7,261,702 B1 | 8/2007 | Alexandre et al. | |
| 7,288,075 B2 | 10/2007 | Parihar et al. | |
| 7,297,102 B2 | 11/2007 | Smith et al. | |
| 7,322,993 B2 | 1/2008 | Metzger et al. | |
| 7,337,781 B2 | 3/2008 | Vassallo | |
| 7,360,432 B2 | 4/2008 | Lehtonen | |
| 7,360,542 B2 | 4/2008 | Nelson et al. | |
| 7,367,340 B2 | 5/2008 | Nelson et al. | |
| 7,401,611 B2 | 7/2008 | Conrad et al. | |
| 7,442,389 B2 | 10/2008 | Quelle et al. | |
| 7,601,164 B2 | 10/2009 | Wu | |
| 7,669,603 B2 | 3/2010 | Knudson et al. | |
| 7,806,908 B2 | 10/2010 | Ruff | |
| 7,850,894 B2 | 12/2010 | Lindh, Sr. et al. | |
| 7,857,829 B2 | 12/2010 | Kaplan et al. | |
| 7,888,119 B2 | 2/2011 | Sugaya et al. | |
| 8,142,422 B2 | 3/2012 | Makower et al. | |
| 8,307,831 B2 | 11/2012 | Rousseau | |
| 8,413,661 B2 | 4/2013 | Rousseau et al. | |
| 2001/0037133 A1 | 11/2001 | Knudson et al. | |
| 2002/0144685 A1 | 10/2002 | Ivanovich et al. | |
| 2003/0004579 A1 | 1/2003 | Rousseau et al. | |
| 2003/0034312 A1 | 2/2003 | Unger et al. | |
| 2003/0149445 A1 | 8/2003 | Knudson et al. | |
| 2003/0149447 A1 | 8/2003 | Morency et al. | |
| 2003/0149488 A1 | 8/2003 | Metzger et al. | |
| 2003/0176875 A1 | 9/2003 | Anderson et al. | |
| 2004/0020492 A1 | 2/2004 | Dubrul et al. | |
| 2004/0020498 A1 | 2/2004 | Knudson et al. | |
| 2004/0028676 A1 | 2/2004 | Klein et al. | |
| 2004/0044366 A1 | 3/2004 | Bonutti et al. | |
| 2004/0102796 A1 | 5/2004 | Hill et al. | |
| 2004/0139975 A1 | 7/2004 | Nelson et al. | |
| 2004/0144395 A1 | 7/2004 | Evans et al. | |
| 2004/0147811 A1 * | 7/2004 | Diederich et al. | 600/207 |
| 2004/0149290 A1 | 8/2004 | Nelson et al. | |
| 2004/0153127 A1 | 8/2004 | Gordon et al. | |
| 2004/0231678 A1 | 11/2004 | Fierro | |
| 2005/0038472 A1 | 2/2005 | Furst | |
| 2005/0082452 A1 | 4/2005 | Kirby | |
| 2005/0092334 A1 | 5/2005 | Conrad et al. | |
| 2005/0115572 A1 | 6/2005 | Brooks et al. | |
| 2005/0121039 A1 | 6/2005 | Brooks et al. | |
| 2005/0159637 A9 | 7/2005 | Nelson et al. | |
| 2005/0165352 A1 | 7/2005 | Henry et al. | |
| 2005/0199248 A1 | 9/2005 | Pflueger et al. | |
| 2005/0203576 A1 | 9/2005 | Sulamanidze et al. | |
| 2005/0251255 A1 | 11/2005 | Metzger et al. | |
| 2005/0267321 A1 | 12/2005 | Shadduck | |
| 2005/0267531 A1 | 12/2005 | Ruff et al. | |
| 2005/0267532 A1 | 12/2005 | Wu | |
| 2005/0267571 A1 | 12/2005 | Spence et al. | |
| 2005/0279365 A1 | 12/2005 | Armijo et al. | |
| 2006/0005843 A9 | 1/2006 | Nelson et al. | |
| 2006/0079935 A1 | 4/2006 | Kolster | |
| 2006/0083767 A1 | 4/2006 | Deusch et al. | |
| 2006/0093644 A1 | 5/2006 | Quelle et al. | |
| 2006/0150986 A1 | 7/2006 | Roue et al. | |
| 2006/0185673 A1 | 8/2006 | Critzer et al. | |
| 2006/0206197 A1 | 9/2006 | Morsi | |
| 2006/0207608 A1 | 9/2006 | Hirotsuka et al. | |
| 2006/0207612 A1 | 9/2006 | Jackson et al. | |
| 2006/0228391 A1 | 10/2006 | Seyedin et al. | |
| 2006/0241339 A1 | 10/2006 | Cook et al. | |
| 2006/0266369 A1 | 11/2006 | Atkinson et al. | |
| 2006/0289015 A1 | 12/2006 | Boucher et al. | |
| 2007/0000497 A1 | 1/2007 | Boucher et al. | |
| 2007/0005109 A1 | 1/2007 | Popadiuk et al. | |
| 2007/0005110 A1 | 1/2007 | Collier et al. | |
| 2007/0102004 A1 | 5/2007 | Nelson et al. | |
| 2007/0102010 A1 | 5/2007 | Lemperle et al. | |
| 2007/0110788 A1 | 5/2007 | Hissong et al. | |
| 2007/0119463 A1 | 5/2007 | Nelson et al. | |
| 2007/0123996 A1 | 5/2007 | Sugaya et al. | |
| 2007/0144531 A1 | 6/2007 | Tomas et al. | |
| 2007/0144534 A1 | 6/2007 | Mery et al. | |
| 2007/0144535 A1 | 6/2007 | Hegde et al. | |
| 2007/0190108 A1 | 8/2007 | Datta et al. | |
| 2007/0204866 A1 | 9/2007 | Conrad et al. | |
| 2007/0209665 A1 | 9/2007 | Gillis et al. | |
| 2007/0227545 A1 | 10/2007 | Conrad et al. | |
| 2007/0233276 A1 | 10/2007 | Conrad et al. | |
| 2007/0246052 A1 | 10/2007 | Hegde et al. | |
| 2007/0256693 A1 | 11/2007 | Paraschac et al. | |
| 2007/0257395 A1 | 11/2007 | Lindh et al. | |
| 2007/0261701 A1 | 11/2007 | Sanders | |
| 2007/0267027 A1 | 11/2007 | Nelson et al. | |
| 2007/0270631 A1 | 11/2007 | Nelson et al. | |
| 2007/0272257 A1 | 11/2007 | Nelson et al. | |
| 2007/0288057 A1 | 12/2007 | Kuhnel | |
| 2007/0295338 A1 | 12/2007 | Loomas et al. | |
| 2007/0295340 A1 | 12/2007 | Buscemi | |
| 2008/0023012 A1 | 1/2008 | Dineen et al. | |
| 2008/0035158 A1 | 2/2008 | Pflueger et al. | |
| 2008/0035160 A1 | 2/2008 | Woodson et al. | |
| 2008/0066764 A1 | 3/2008 | Paraschac et al. | |
| 2008/0066765 A1 | 3/2008 | Paraschac et al. | |

(56) References Cited

U.S. PATENT DOCUMENTS

| | | | |
|---|---|---|---|
| 2008/0066767 A1 | 3/2008 | Paraschac et al. |
| 2008/0066769 A1 | 3/2008 | Dineen et al. |
| 2008/0078411 A1 | 4/2008 | Buscemi et al. |
| 2008/0146868 A1 | 6/2008 | Robert et al. |
| 2008/0167614 A1 | 7/2008 | Tolkowsky et al. |
| 2008/0199824 A1 | 8/2008 | Hargadon |
| 2008/0208265 A1 | 8/2008 | Frazier et al. |
| 2008/0221684 A1 | 9/2008 | Nelson et al. |
| 2008/0312688 A1 | 12/2008 | Nawrocki et al. |
| 2009/0025734 A1 | 1/2009 | Doelling et al. |
| 2009/0078411 A1 | 3/2009 | Kenison et al. |
| 2009/0165803 A1 | 7/2009 | Bhat et al. |
| 2009/0299472 A1* | 12/2009 | Huang ............... A61F 2/52 623/7 |
| 2010/0023055 A1 | 1/2010 | Rousseau |
| 2010/0024830 A1 | 2/2010 | Rousseau |
| 2010/0030011 A1 | 2/2010 | Weadock |
| 2010/0037901 A1 | 2/2010 | Rousseau |
| 2010/0080791 A1 | 4/2010 | Rousseau |
| 2010/0106246 A1 | 4/2010 | Rousseau |
| 2010/0108077 A1 | 5/2010 | Lindh |
| 2010/0132719 A1 | 6/2010 | Jacobs et al. |
| 2010/0137794 A1 | 6/2010 | Knudson et al. |
| 2010/0137905 A1 | 6/2010 | Weadock et al. |
| 2010/0158854 A1 | 6/2010 | Puisais |
| 2010/0163056 A1 | 7/2010 | Tschopp et al. |
| 2010/0211184 A1 | 8/2010 | Rousseau |
| 2010/0234794 A1 | 9/2010 | Weadock |
| 2010/0234946 A1 | 9/2010 | Rousseau |
| 2010/0256443 A1 | 10/2010 | Griguol |
| 2010/0294284 A1 | 11/2010 | Hohenhorst et al. |
| 2010/0319710 A1 | 12/2010 | Sharkawy et al. |
| 2011/0054522 A1 | 3/2011 | Lindh et al. |
| 2011/0100376 A1 | 5/2011 | Rousseau |
| 2011/0100377 A1 | 5/2011 | Weadock et al. |
| 2011/0100378 A1 | 5/2011 | Rousseau |
| 2011/0144558 A1 | 6/2011 | Rousseau |
| 2011/0174315 A1 | 7/2011 | Zhang et al. |
| 2011/0178439 A1 | 7/2011 | Irwin et al. |
| 2011/0238111 A1 | 9/2011 | Frank |
| 2011/0245850 A1 | 10/2011 | van der Burg et al. |
| 2012/0123449 A1 | 5/2012 | Schaller et al. |
| 2012/0160249 A1 | 6/2012 | Thomason et al. |
| 2012/0245629 A1 | 9/2012 | Gross et al. |
| 2013/0074849 A1 | 3/2013 | Rousseau et al. |
| 2013/0098371 A1 | 4/2013 | Rousseau et al. |
| 2013/0118505 A1 | 5/2013 | Rousseau et al. |
| 2013/0133669 A1 | 5/2013 | Rousseau |
| 2013/0150872 A1 | 6/2013 | Rousseau |
| 2013/0174857 A1 | 7/2013 | Rousseau et al. |
| 2013/0186412 A1 | 7/2013 | Weadlock et al. |
| 2013/0319427 A1 | 12/2013 | Sung et al. |

FOREIGN PATENT DOCUMENTS

| | | |
|---|---|---|
| CN | 102198010 | 9/2011 |
| DE | 10245076 | 4/2004 |
| EP | 2145587 | 1/2010 |
| EP | 2386252 A1 | 11/2011 |
| EP | 2517633 | 10/2012 |
| FR | 2651113 | 3/1991 |
| JP | 2001145646 | 5/2001 |
| JP | 2003265621 | 9/2003 |
| RU | 2005447 | 1/1994 |
| RU | 2202313 | 4/2003 |
| SU | 927236 | 5/1982 |
| SU | 1697792 | 12/1991 |
| WO | 199713465 | 4/1997 |
| WO | 1999000058 | 1/1999 |
| WO | 2000066050 | 11/2000 |
| WO | 2001021107 | 3/2001 |
| WO | 2003/096928 | 11/2003 |
| WO | 2004016196 | 2/2004 |
| WO | 2004/020492 | 3/2004 |
| WO | 2004/021869 | 3/2004 |
| WO | 2004021870 | 3/2004 |
| WO | 2004060311 | 7/2004 |
| WO | 2004084709 | 10/2004 |
| WO | 2004/103196 | 12/2004 |
| WO | 2005046554 | 5/2005 |
| WO | 2005051292 | 6/2005 |
| WO | 2005082452 | 9/2005 |
| WO | 2005122954 | 12/2005 |
| WO | 2006012188 | 2/2006 |
| WO | 2006072571 | 7/2006 |
| WO | 2006108145 | 10/2006 |
| WO | 2007056583 | 5/2007 |
| WO | 2007075394 | 7/2007 |
| WO | 2007132449 | 11/2007 |
| WO | 2007134005 | 11/2007 |
| WO | 2007146338 | 12/2007 |
| WO | 2007149469 | 12/2007 |
| WO | 2008118913 | 10/2008 |
| WO | 2009023256 | 2/2009 |
| WO | 2009036094 | 3/2009 |
| WO | 2010019376 | 2/2010 |
| WO | 2010/035303 | 4/2010 |
| WO | 2010065341 | 6/2010 |
| WO | 2012004758 | 1/2012 |
| WO | 2012/041205 | 4/2012 |
| WO | 2012/064902 | 5/2012 |
| WO | 2012170468 | 12/2012 |

OTHER PUBLICATIONS

Wassmuth et al., "Cautery-assisted palatal stiffening operation for the treatment of obstructive sleep apnea syndrome", Otolaryngology—Head and Neck Surgery, vol. 123 (1), pp. 55-60 (2000).

The Pillar Palatal Implant System, Restore Medical, Inc., www.restoremedical.com, 2 pp. (2008).

Repose Genioglossus Advancement, Influent Medical, www.-influent.com, 1 p. (2008).

Cole et al., "Snoring: A Review and a Reassessment", J. of Otolaryngology, pp. 303-306 (1995).

Huang et al., "Biomechanics of snoring", Endeavour, vol. 19(3): pp. 96-100 (1995).

Pang, Kenny et al., "Tongue Suspension Suture in Obstructive Sleep Apnea", Operative Techniques in Otolarynogology, vol. 17, No. 4, Dec. 2006, pp. 252-256.

Schwab et al., "Upper airway and soft tissue changes induced by CPAP in normal subject", Am. J. Respit. Crit. Care Med., vol. 154, No. 4, Oct. 1996, pp. 1106-1116.

Schwartz et al., "Effects of electrical stimulation to the soft palate on snoring and obstructive sleep apnea", J. Prosthetic Dentistry, pp. 273-281 (1986).

Shamsuzzaman et al., "Obstructive Sleep Apnea; Implications for Cardiac and Vascular Disease", JAMA vol. 290 (14); pp. 1906-1914.

Teles et al., "Use of Palatal Lift Prosthesis on Patient Submitted to Maxillectomy: A Case Report", Applied Cancer Res. 2005, vol. 25(3), pp. 151-154.

The Advance System, Aspire Medical, Inc. www.aspiremedical.com, 3 pp (2008).

Vicente et al., "Tongue-Base Suspension in Conjunction with Uvulopapatopharyngoplasty for Treatment of Severe Obstructive Sleep Apnea: Long-term Follow-Up Results", The Laryngoscope, vol. 115(7), pp. 1223-1227 (2006).

Wiltfang et al., "First results on daytime submandibular electrostimulation of suprahyoidal muscles to prevent night-time hypopharyngeal collapse in obstructive sleep apnea syndrom", Intl J. of Oral & Maxillofacial Surgery, pp. 21-25 (1999).

Notification of Transmittal of the International Search Report and the Written Opinion of the International Search Authority or the Declaration dated Feb. 3, 2010; PCT/US2009/051921; International Filing Date: Jul. 28, 2009.

Notification of Transmittal of the International Search Report and the Written Opinion of the International Search Authority or the Declaration dated May 25, 2010; PCT/US2010/023152; International Filing Date: Apr. 2, 2010.

(56) References Cited

OTHER PUBLICATIONS

International Search Report dated Nov. 4, 2009 for International Patent Application No. PCT/US2009/052126.
International Search Report dated Dec. 21, 2009 for International Patent Application No. PCT/US2009/057661.
International Search Report dated Dec. 22, 2009 for International Patent Application No. PCT/US2009/061223.
International Search Report dated Apr. 29, 2010 for International Patent Application No. PCT/US2009/065293.
International Search Report dated May 25, 2010 for International Patent Application No. PCT/US2010/025778.
International Search Report for International Patent Application No. PCT/US2012/061569, dated Apr. 9, 2013, 6 pp.
International Search Report for International Patent Application No. PCT/US2012/067708, dated Apr. 2, 2013, 4 pp.
Database WPI Week 198312, Thomson Scientific, Londo, GB; AN 1983-D9513K XP 002693421, —& SU 927 236 A1 (Petrozazodsk Univ.), May 15, 1982 (May 15, 1982) abstract (see figures 7 & 8), dated Mar. 12, 2013, 1p.
Schleef et al., "Cytokine Activation of Vascular Endothelium, Effects on Tissue-Type 1 Plasminogen Activator Inhibitor, " The Journal of Biological Chem., vol. 263, No. 12, pp. 5797-5803 (1988).
International Search Report for International Patent Application No. PCT/US2009/061455, dated Dec. 29, 2009, 5 pp.
International Search Report for International Patent Application No. PCT/US2009/052110, dated Jan. 21, 2010, 6 pp.
International Search Report for International Patent Application No. PCT/US2010/023152, dated May 25, 2010, 4 pp.
International Search Report for International Patent Application No. PCT/US2010/52628, Dated Jan. 14, 2011, 4 pp.
International Search Report for International Patent Application No. PCT/US2010/052644, dated Jan. 20, 2011, 4 pp.
International Search Report for International Patent Application No. PCT/US2010/052649, dated Jan. 24, 2011, 6 pp.
International Search Report for International Patent Application No. PCT/US2010/059673, dated Feb. 28, 2011, 3 pp.
International Search Report for International Patent Application No. PCT/US2012/056577, dated Nov. 27, 2012, 4 pp.
International Search Report for PCT/US2013/043238, dated Oct. 2, 2013, 7 pp.
Friedman et al., A System and Method for Inserting a Medical Device for Treatment of Sleep Apnea via the Nasal Passage, and Device Therefor, Dec. 29, 2008, U.S. Appl. No. 61/203,758, p. 8 & p. 6/8.
Medtronic AIRvance System for Obstructive Sleep Apnea, http://www.medtronic.com/for-healthcare-professionals/products-therapies/ear-nose-throat/sleep-disordered-breathing-products/airvance-system-for-obstructive-sleep-apnea/index.htm, Oct. 9, 2013, 3 pages.

* cited by examiner

FIG. 4A
FIG. 4B
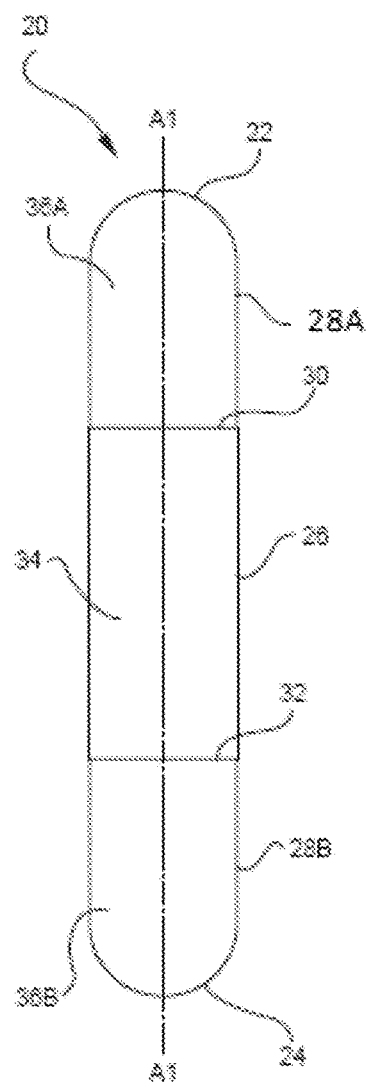
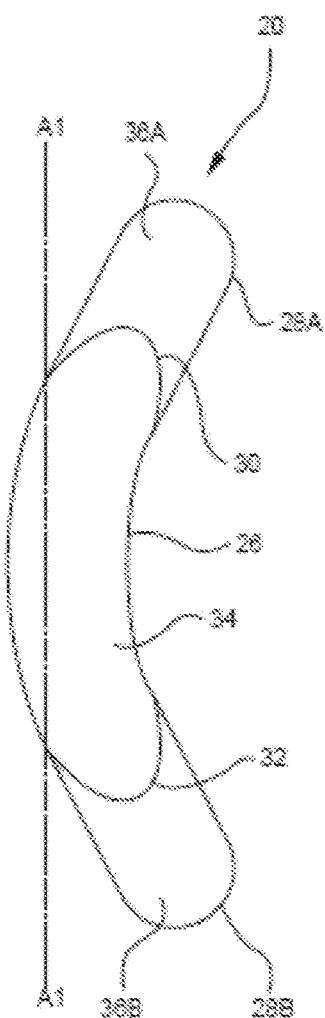

FLEXIBLE IMPLANTS HAVING INTERNAL VOLUME SHIFTING CAPABILITIES FOR TREATING OBSTRUCTIVE SLEEP APNEA

BACKGROUND OF THE INVENTION

Field of the Invention

The present invention generally relates to treating sleep disorders, and more specifically relates to systems, devices and methods for treating patients suffering from obstructive sleep apnea.

Description of the Related Art

Obstructive sleep apnea (OSA) is caused by a blockage of the airway, which usually occurs when the soft tissue in the throat collapses and closes during sleep. The blockage can occur in a portion of the pharyngeal lumen and may include obstructions formed by the collapse of the tongue against the posterior wall of the pharynx, the collapse of the lateral pharyngeal walls, and the combined collapse of the tongue with impingement of the soft palate, particularly the posterior portion of the soft palate including the uvula. During each apnea event, the brain briefly arouses the sufferer in order to initiate the resumption of breathing. This type of sleep, however, is extremely fragmented and of poor quality.

According to the National Institutes of Health, OSA affects more than twelve million Americans. When left untreated, OSA may result in high blood pressure, cardiovascular disease, weight gain, impotency, headaches, memory problems, job impairment, and/or motor vehicle crashes. Despite the seriousness of OSA, a general lack of awareness among the public and healthcare professionals results in the vast majority of OSA sufferers remaining undiagnosed and untreated.

There have been a number of efforts directed to treating OSA. For example, devices for electrically stimulating the soft palate to treat snoring and obstructive sleep apnea are disclosed in U.S. Pat. Nos. 5,284,161 and 5,792,067. Use of these devices have had mixed results because they require patient adherence to a strict regimen of use, subject the patient to discomfort during sleep, and result in repeated arousal of the patient.

Another treatment, commonly referred to as continuous positive airway pressure (CPAP), delivers air into a patient's airway through a specially designed nasal mask or pillow. The flow of air creates positive pressure when the patient inhales to keep the airway open. CPAP is considered by many to be an effective non-surgical treatment for the alleviation of snoring and obstructive sleep apnea, however, patients complain about discomfort caused by the mask and hoses, including bloating, nasal drying, and dry eyes. As a result, patient compliance for CPAP is only about 40%.

Surgical treatments have also been used to treat OSA. One such treatment is referred to as uvulopalatopharyngoplasty, which involves removing about 2 cm of the trailing edge of the soft palate to reduce the soft palate's ability to flutter between the tongue and the pharyngeal wall. Another procedure uses a surgical laser to create scar tissue on the surface of the soft palate, which reduces the flexibility of the soft palate for reducing snoring and/or closing of the air passage. Yet another procedure, commonly referred to as cautery-assisted palatal stiffening operation (CAPSO), is an office-based procedure performed under local anesthesia whereby a midline strip of soft palate mucosa is removed, and the wound is allowed to heal for stiffening the palate.

Surgical procedures such as those mentioned above continue to have problems. Specifically, the area of tissue that is surgically treated (i.e., removal of palatal tissue or scarring of palatal tissue) is often larger than is necessary to treat the patient's condition. In addition, the above-mentioned surgical procedures are often painful with extended, uncomfortable healing periods. For example, scar tissue on the soft palate may present a continuing irritant to the patient. Furthermore, the above procedures are not reversible in the event of adverse side effects.

Another surgical procedure for treating OSA uses several braided PET cylinders that are implanted in tissue to make the tissues of the tongue or uvula more rigid and less prone to deflection. The Pillar™ Palatal Implant System sold by Restore Medical of St. Paul, Minn. consists of cylindrical-shaped elements of braided polyester filaments that are implanted in the soft palate for reducing the incidence of airway obstructions in patients suffering from mild to moderate OSA. Use of the Pillar device may result in adverse side effects, including extrusion of the cylindrical-shaped elements, infection, and patient discomfort.

Another implant system, sold under the trademark REPOSE™ by InfluENT of Concord, N.H., uses a titanium bone screw that is inserted into the posterior aspect of the mandible at the floor of the mouth. A loop of suture is passed through the tongue base and attached to the mandibular bone screw. The Repose™ procedure achieves a suspension or hammock of the tongue base making it less likely for the base of the tongue to prolapse during sleep. Due to the high activity of the tongue during wakefulness, however, the suture component of this device may act as a "cheese cutter" to the tongue, causing device failure and requiring subsequent removal.

Another effort for treating OSA involves creating an auxiliary airway for bypassing the clogged portion of the main airway. In one embodiment of commonly assigned U.S. patent application Ser. No. 12/182,402, filed Jul. 30, 2008, the disclosure of which is hereby incorporated by reference herein, an auxiliary airway is formed by implanting an elongated conduit beneath a pharyngeal wall of the pharynx. The elongated conduit has a proximal end in communication with a first region of the pharynx, a distal end in communication with a second region of the pharynx, and an intermediate section extending beneath the pharyngeal wall for bypassing an oropharynx region of the pharynx.

Magnets have also been used for treating OSA. For example, in one embodiment of commonly assigned U.S. patent application Ser. No. 12/183,955, filed Jul. 31, 2008, the disclosure of which is hereby incorporated by reference herein, a magnetic implant includes a bone anchor, a first magnet coupled to the bone anchor, a tongue anchor, a second magnet coupled to the tongue anchor, and a support for aligning the first and second magnets so that a repelling force is generated between the magnets for urging the second magnet away from the first magnet and toward the bone anchor. The support maintains the first magnet at a fixed distance from the bone anchor, aligns the first magnet with the second magnet, and guides movement of the first and second magnets. The magnetic implant disclosed in one or more embodiments of the '955 application does not have a hard stop so as to avoid the "cheese-cutter" effect observed when using implants having a hard stop.

In spite of the above advances, there remains a need for additional systems, devices and methods for treating OSA through minimally invasive approaches that provide long-term efficacious results, that encourage patient compliance, and that minimize patient discomfort.

SUMMARY OF THE INVENTION

In one embodiment, an implant for treating obstructive sleep apnea includes a first chamber containing an incompressible fluid, a second chamber containing a compressible fluid, and a flexible diaphragm separating the first and second chambers. The incompressible fluid within the first chamber is in communication with the compressible fluid within the second chamber via the flexible diaphragm. In one embodiment, the first chamber has a first volume that remains constant during flexing of the implant and the second chamber has a second volume that changes during flexing of the implant. In one embodiment, the flexible diaphragm is extendible into the second chamber for reducing the second volume of the second chamber and compressing the compressible fluid within the second chamber. Application of an external force upon the first chamber preferably extends the flexible diaphragm into the second chamber for compressing the compressible fluid within the second chamber.

The implant disclosed herein is desirably adapted for implantation within the soft tissue of an oropharyngeal airway so as to control the tissue and prevent the tissue from collapsing during sleep. The implant may be implantable within a tongue, a soft palate, or a pharyngeal wall. In one embodiment, a plurality of implants may be used. In one embodiment, one or more implants may be implanted in a first soft tissue location such as the tongue, and one or more implants may be implanted in a second soft tissue location such as the soft palate or a pharyngeal wall.

In one embodiment, an implant for treating obstructive sleep apnea is preferably made of durable, biocompatible polymeric or elastomeric materials. In one embodiment, the incompressible fluid within the first chamber may be liquid, water, saline solution or a flowable gel. The compressible fluid within the second chamber may be a gas such as nitrogen or air.

In one embodiment, the implant preferably has a longitudinal axis that is alignable with an anterior-posterior, transverse, vertical, or horizontal axis of a patient. In one embodiment, the longitudinal axis of the implant may be angled relative to one of the anterior-posterior, transverse, vertical, or horizontal axes of the patient. The number of implants utilized and the particular placement, angulation, and/or orientation of the implant(s) preferably depends upon the particular tissue support needs of a patient.

In one embodiment, the implant is adapted to flex between a substantially straight configuration and a curved configuration. The incompressible and compressible fluids desirably cooperate to provide for less resistance to flexing during an initial flexing stage and more resistance to flexing during a later flexing stage.

In one embodiment, the implant is adapted to flex between a preformed shape such as curvilinear, to a straightened condition.

In one embodiment, an implant for treating obstructive sleep apnea includes a central chamber containing an incompressible fluid, a first outer chamber located adjacent a first end of the central chamber and containing a first compressible fluid, and a first flexible diaphragm separating the first end of the central chamber and the first outer chamber. The implant desirably includes a second outer chamber located adjacent a second end of the central chamber and containing a second compressible fluid, and a second flexible diaphragm separating the second end of the central chamber and the second outer chamber.

In one embodiment, the incompressible fluid within the central chamber is preferably in communication with the first compressible fluid via the first flexible diaphragm and is in communication with the second compressible fluid via the second flexible diaphragm. The first chamber preferably has a first volume that remains constant when an external force is applied to the implant and the first and second outer chambers have respective volumes that are changeable when the external force is applied to the implant.

In one embodiment, the first flexible diaphragm is desirably extendible into the first outer chamber for reducing the volume of the first outer chamber and compressing the first compressible fluid within the first outer chamber, and the second flexible diaphragm is extendible into the second outer chamber for reducing the volume of the second outer chamber and compressing the second compressible fluid within the second outer chamber. The deformation of the diaphragm within the outer chamber accommodates volume shifting without increasing the external geometry of the device.

In one embodiment, an implant for treating obstructive sleep apnea includes a first flexible chamber containing an incompressible fluid, the first chamber defining a first volume that remains constant during flexing of the implant, and a second chamber containing a compressible fluid, the second chamber defining a second volume that changes during flexing of the implant. The implant preferably includes a flexible diaphragm separating the first and second chambers, whereby the incompressible fluid within the first chamber is in communication with the compressible fluid within the second chamber via the flexible diaphragm. In one embodiment, the compressible fluid within the second chamber provides less resistance to flexing during a significant portion of flexure and more resistance to flexing during a later flexing stage. Additionally, the compression of the compressible fluid in the second chamber accommodates bending of the device without lengthening of the overall device. In one embodiment, the force required to flex the implant remains relatively low and constant during initial flexing of the implant and the resistive force to flexing increases significantly and more rapidly during further flexing of the implant.

In one embodiment, as the flexible diaphragm extends into the second chamber (e.g. during flexing of the implant), the pressure level of the compressible fluid maintains the rigidity of the implant during a significant portion of flexure. As the pressure level of the compressible fluid is reduced (e.g. during straightening of the implant), the rigidity of the implant is reduced.

In one embodiment, an implant for treating obstructive sleep apnea may not have a valve and may simply transfer fluid from one compartment into a distensible region of the device when compressed. In this particular embodiment, the implant device preferably provides support immediately upon placement, however, the distensible region of the compartment controls the resistance to fluid motion, which provides for an extended and controllable elastic response of the device without reliance upon deformation within a solid-state material subjected to bending.

In one embodiment, the implant may have a surface adapted to promote tissue in-growth. The tissue in-growth promoting surface is desirably selected from a group of outer surfaces including a textured surface, a porous surface, a braided surface, a mesh surface, a fleece surface, and a coating such as hydroxyapatite for inducing bone or tissue in-growth.

Although the present invention is not limited by any particular theory of operation, it is believed that the implant provides a number of benefits over prior art devices. First, the implant may be removed from a patient if efficacious results are not obtained. Second, the implant preferably provides the minimum necessary support to the soft tissue of the oropharyngeal airway when a patient is asleep. Since the implant is made to provide similar loads under significant deflection, it minimizes the chance of affecting speech or swallowing. In addition, the implant of the present invention preferably controls the shape of the soft tissue without requiring a hard anchoring point so as to minimize the chance of the implant tearing out or pulling through the tissue.

In the event of forceful swallowing during sleep, the implant may deform temporarily to allow swallowing. After the muscular activity related to swallowing subsides, the implant preferably resumes the preferred shaped so as to provide support and re-shaping of the relaxed tissues.

In one embodiment, an implant is fabricated from flexible film materials to minimize patient awareness of the implanted device.

These and other preferred embodiments of the present invention will be described in more detail below.

BRIEF DESCRIPTION OF THE DRAWING

FIG. 4A shows an implant for treating obstructive sleep apnea, in accordance with one embodiment of the present invention.

FIG. 4B shows the implant of FIG. 4A after being flexed, in accordance with one embodiment of the present invention.

DETAILED DESCRIPTION

Figure 1:
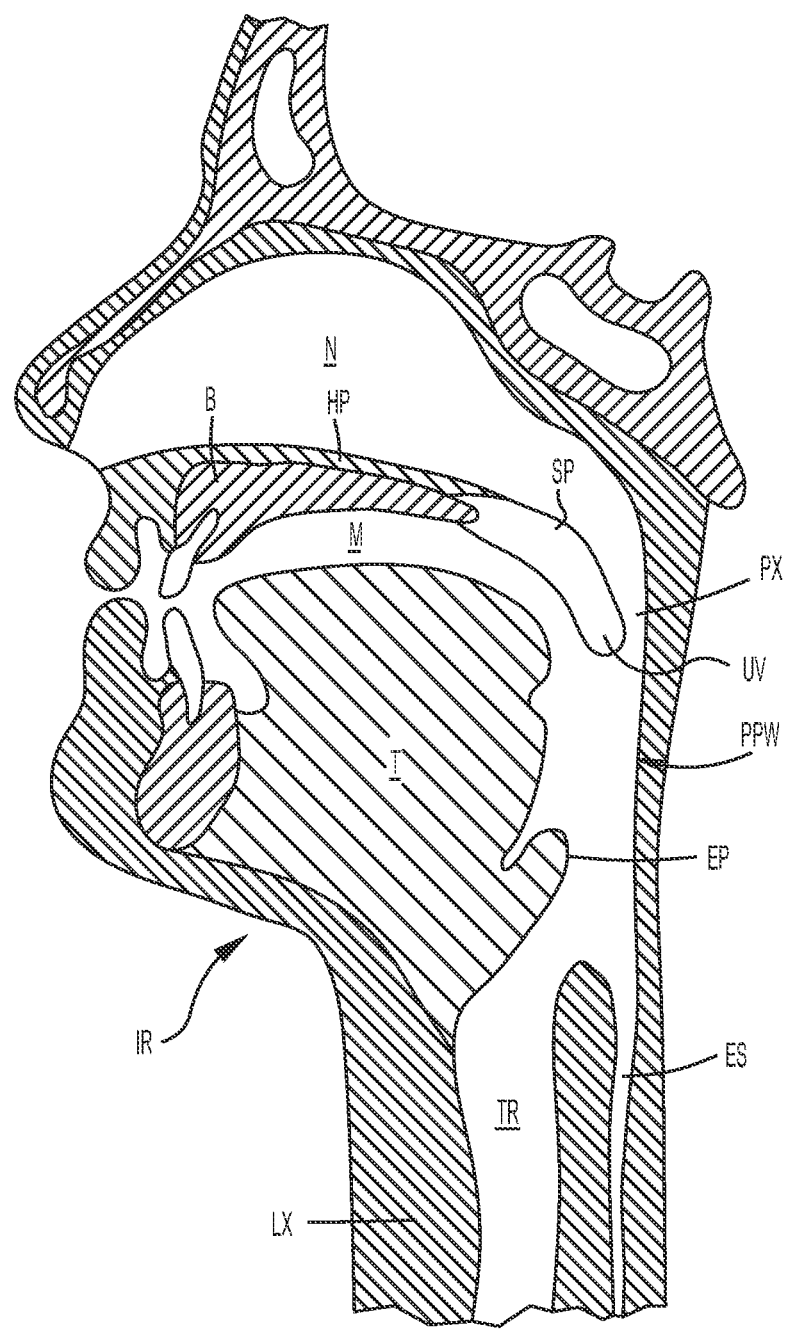
FIG. 1 shows a cross-sectional view of a human head including a nasal cavity and a pharynx.

FIG. 1 shows a cross-section of a human head with anatomical structures including the nasal cavity N, bone B of the hard palate HP, the soft palate SP including the uvula UV at the posterior end thereof, the mouth M, the tongue T, the trachea TR, the epiglottis EP, the esophagus ES, and the posterior pharyngeal wall PPW.

Figure 2:
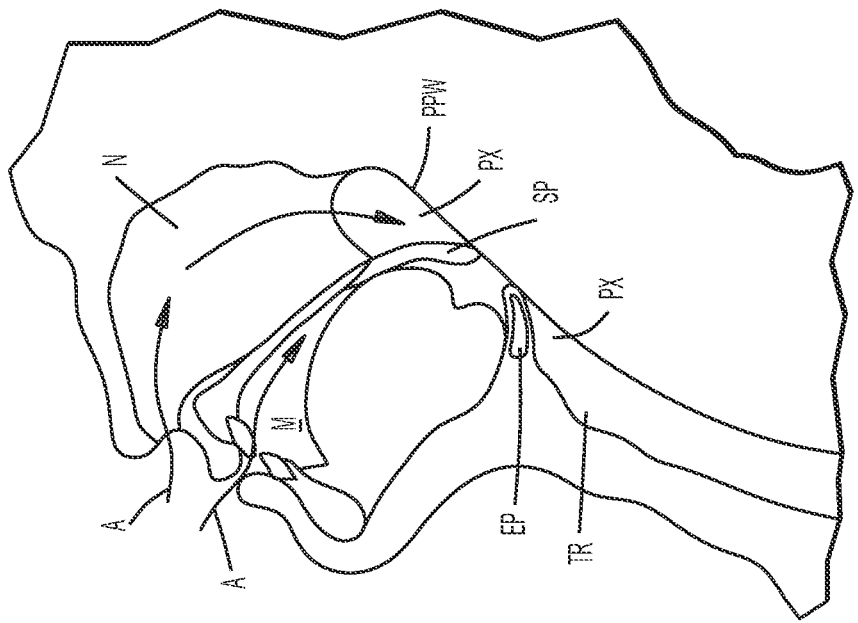
FIG. 2 shows a cross-sectional view of the nasal cavity and the pharynx of a human during normal breathing.

In a human body, an air filled space between the nasal cavity N and the larynx LX is referred to as the upper airway. The most critical part of the upper airway associated with sleep disorders is the pharynx PX. Referring to FIG. 2, the pharynx has three different anatomical levels. The nasopharynx NP is the upper portion of the pharynx located in the back of the nasal cavity N. The oropharynx OP is the intermediate portion of the pharynx containing the soft palate SP, the epiglottis EP, and the curve at the back of the tongue T. The hypopharynx HP is the lower portion of the pharynx located below the soft tissue of the oropharynx OP. The oropharynx OP is the section of the pharynx that is most likely to collapse due to the high prevalence of soft tissue structure, which leaves less space for airflow. The hypopharynx HP lies below the aperture of the larynx and behind the larynx, and extends to the esophagus.

As is well known to those skilled in the art, the soft palate and the tongue are both flexible structures. The soft palate SP provides a barrier between the nasal cavity N and the mouth M. In many instances, the soft palate SP is longer than necessary and extends a significant distance between the back of the tongue T and the posterior pharyngeal wall PPW. The midline posterior end of the soft palate is referred to as the uvula, which is the soft tissue that extends downward from the soft palate over the back of the tongue.

Although the muscles relax throughout the body during sleep, most of the muscles of the respiratory system remain active. During inhalation, the diaphragm contracts and causes negative pressure to draw air A into the nasal cavity N and the mouth M. The air then flows past the pharynx PX, through the trachea TR and into the lungs. The negative pressure causes the tissue of the upper airway to deform slightly, which narrows the airway passage. In apneic patients, the soft palate SP, the tongue T, and/or the epiglottis EP collapse against the posterior pharyngeal wall PPW to block airflow into the trachea. As the airway narrows, airflow through the pharynx becomes turbulent, which causes the soft palate SP to vibrate, generating a sound commonly known as snoring.

During sleep, humans typically experience brief obstructions of airflow and/or small decreases in the amount of airflow into the trachea and lungs. An obstruction of airflow for more than ten seconds is referred to as apnea. A decrease in airflow by more than fifty percent is referred to as hypopnea. The severity of sleep disorders is measured by the number of apneas and hypopneas that occur during every hour of sleep.

If apnea or hypopnea occurs more than five times per hour, most medical personnel diagnose the individual as having an upper airway resistance problem. Many of these patients often exhibit symptoms related to sleep disorders including sleepiness during the day, depression, and difficulty concentrating.

Individuals having ten or more episodes of apnea or hypopnea during every hour of sleep are diagnosed as having obstructive sleep apnea syndrome. As the airway is obstructed, the individual makes repeated attempts to force inhalation. Many of these episodes are silent and are characterized by movements of the abdomen and chest wall as the individual strains to draw air into the lungs. Typically, episodes of apnea may last a minute or more. During this time, oxygen levels in the blood will decrease. Ultimately, the obstruction may be overcome by the individual generating a loud snore or by the patient awakening with a choking feeling.

Referring to FIG. 2, when an individual is awake, the back of the tongue T and the soft palate SP maintain their shape and tone due to their respective internal muscles. As a result, the airway A through the pharynx remains open and unobstructed. During sleep, however, the muscle tone decreases and the posterior surface of the tongue and the soft palate become more flexible and distensible.

Figure 3:
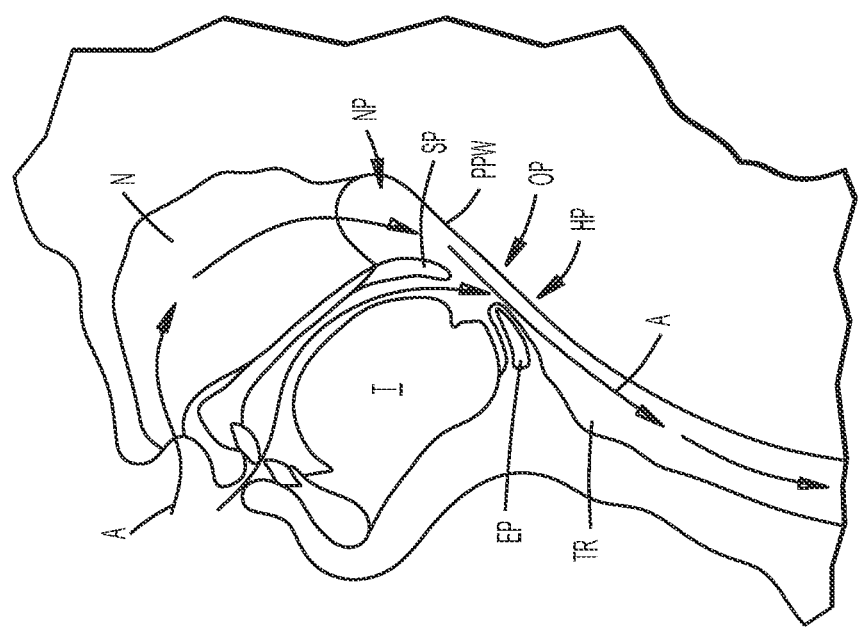
FIG. 3 shows a cross-sectional view of the nasal cavity and the pharynx of a human during an obstructive sleep apnea episode.

Referring to FIG. 3, without normal muscle tone to keep their shape and to keep them in place either alone or as a group, the posterior surface of the tongue T, the epiglottis EP, and the soft palate SP tend to easily collapse to block the airway A. During sleep, the posterior end of the tongue T may block the airway A between the nasal passages N and the upper end of the trachea TR. The soft palate SP may also relax and have the uvula UV slide between the back of the tongue T and the posterior pharyngeal wall PPW. Additionally, the relaxed musculature within the soft tissues of the posterior and lateral walls of the pharynx PX may enable the soft tissues to collapse inward due to the low inspiratory pressures during breathing.

Referring to FIG. 4A, in one embodiment of the present invention, an implant 20 for treating obstructive sleep apnea includes a first end 22, a second end 24 and a longitudinal axis $A_1$ extending along the length of the implant between the first and second ends 22, 24. The implant 20 is desirably made of one or more biocompatible, non-resorbable materials that are durable and safe for use in humans. The implant 20 may be made of a wide variety of biocompatible materials including silicones, polyurethanes, polyesters, PVDF, nylons or other elastomeric materials or combinations thereof. In one embodiment, the implant 20 is preferably flexible and may be at least partially filled with one or more fluids. When not subjected to external forces, the implant 20 normally retains and/or assumes the substantially straight or undeflected shape shown in FIG. 4A.

In one embodiment, the implant 20 preferably includes a central chamber 26 and a pair of outer chambers 28A, 28B. In one embodiment, the implant 20 preferably includes a first flexible diaphragm 30 that separates the central chamber 26 from the first outer chamber 28A, and a second flexible diaphragm 32 that separates the central chamber 26 from the second outer chamber 28B. In one embodiment, the central chamber 26 is desirably filled with an incompressible fluid 34 such as liquid, water, saline, flowable gel, etc. The outer chambers 28A, 28B are desirably filled with a vacuum or a low pressure compressible fluid 36A, 36B such as air, gas, nitrogen, or a combination thereof.

Referring to FIG. 4B, in one embodiment, when subjected to external forces, the implant 20 may flex relative to the longitudinal axis $A_1$-$A_1$. In one embodiment, as the implant 20 flexes, the central chamber 26 of the implant 20 that contains the incompressible fluid 34 is desirably elongated and/or distorted. As the central chamber 26 is elongated and/or distorted, the incompressible fluid 26 within the central chamber 26 forces the first and second flexible diaphragms 30, 32 to extend into the respective first and second outer chambers 28A, 28B. As the flexible diaphragms 30, 32 extend outwardly into the outer chambers 28A, 28B, the compressible fluid 36A, 36B located within the respective outer chambers 28A, 28B is compressed. Compression of the fluid 36A, 36B within the outer chambers 28A, 28B increases the pressure within the outer chambers slightly, which minimally reduces the flexibility of the implant 20.

The flexible fluid filled implant shown and described above in FIGS. 4A and 4B may be implanted in the soft tissue of an upper airway, such as the tongue, the soft palate, and/or the pharyngeal wall. More than one of the flexible fluid implants may be utilized to treat symptoms associated with obstructive sleep apnea. The one or more implants may be aligned with an anterior-posterior, vertical, transverse or horizontal axis of a patient. The one or more implants may also be positioned to extend at any selected angle relative to anterior-posterior, vertical, transverse or horizontal axes of a patient.

Figure 5A:
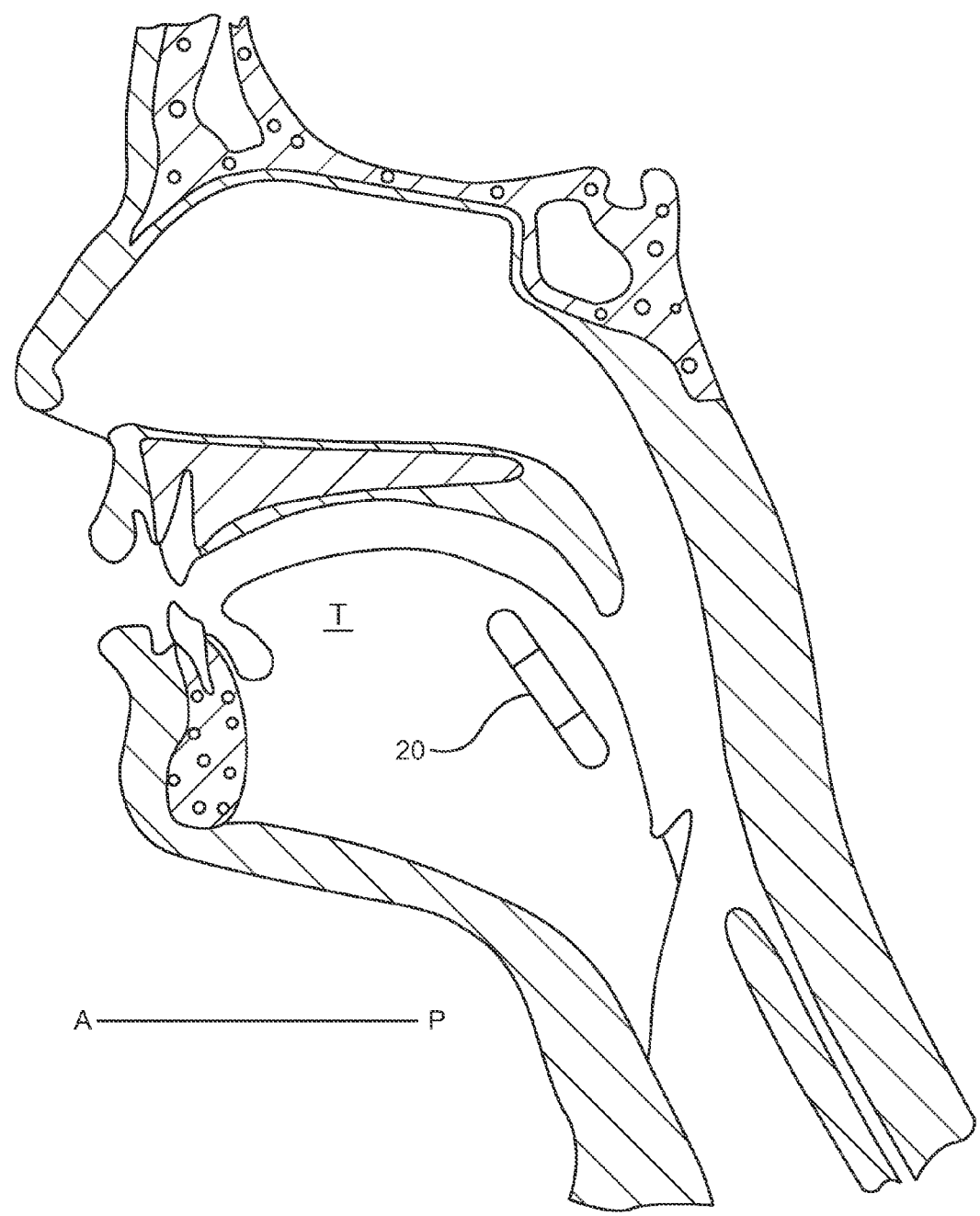
FIG. 5A shows the implant of FIGS. 4A and 4B implanted in a tongue, in accordance with one embodiment of the present invention.

Referring to FIG. 5A, in one embodiment, a flexible implant 20 as described herein is implantable within the base of a tongue T. In one embodiment, the flexible implant 20 desirably extends along an anterior-posterior axis A-P of the tongue T. Although only one implant is shown in FIG. 5A, in one embodiment, two or more implants may be implanted within the tongue.

Figure 5B:
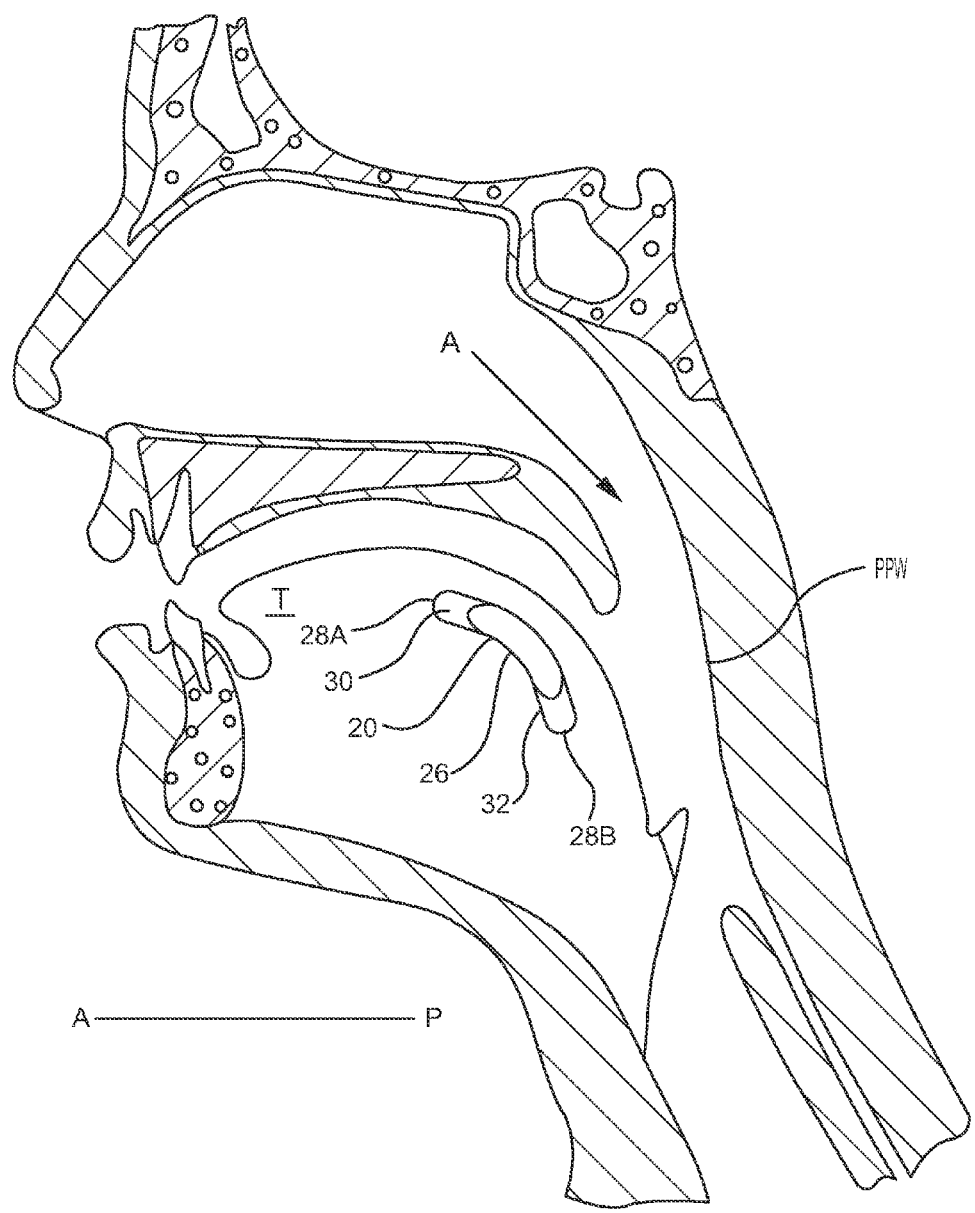
FIG. 5B shows the implant of FIG. 5A during flexing of the implant.

Referring to FIG. 5B, during sleep, muscles of the upper airway may relax. As a result, the base of the tongue T may relax and move toward the opposing posterior pharyngeal wall PPW. As the back of the tongue T moves toward the posterior pharyngeal wall, the upper airway A may be closed so as to cause obstructive sleep apnea episodes.

In one embodiment, as the tongue T relaxes during sleep, the posterior portion of the tongue may relax and move toward the opposing posterior pharyngeal wall PPW, which may at least partially close the airway A. In response to the forces applied upon the implant 20 by the relaxing tongue T, the implant 20 may flex and bend as shown in FIG. 5B. Flexure of the implant 20 preferably causes the central chamber 26 to elongate, which, in turn, forces the first and second flexible diaphragms 30, 32 to extend into the respective outer chambers 28A, 28B. As the first and second flexible diaphragms 32, 34 extend into the outer chambers 28A, 28B, the compressible fluid 36A, 36B within the outer chambers 28A, 28B is compressed, which increases the pressure of the fluid 36A, 36B slightly which causes a minimal reduction in the flexibility of the implant 20. The implant will now provide sufficient resistance to further relaxation of the tongue toward the poster pharyngeal wall PPW so as to avoid an obstructive sleep apnea episode. In the wakeful condition, the normal muscular motion of the tongue is only slightly affected by the implant as the forces required to deform the implant are similar throughout the typical deflection.

FIGS. 5A and 5B show one embodiment of the present invention wherein the implant 20 is implanted within the tongue and extends generally along an anterior-posterior axis of a patient. In other embodiments, however, the implant may be implanted in a direction that is transverse to the anterior-posterior axis. In one embodiment, the flexible fluid filled implant 20 may have a longitudinal axis that extends laterally and substantially perpendicular to the anterior-posterior axis of a patient. The implant may also be implanted so that it extends along a vertical axis of a patient, a horizontal axis of a patient, or any selected angle between vertical and horizontal.

Figure 6:
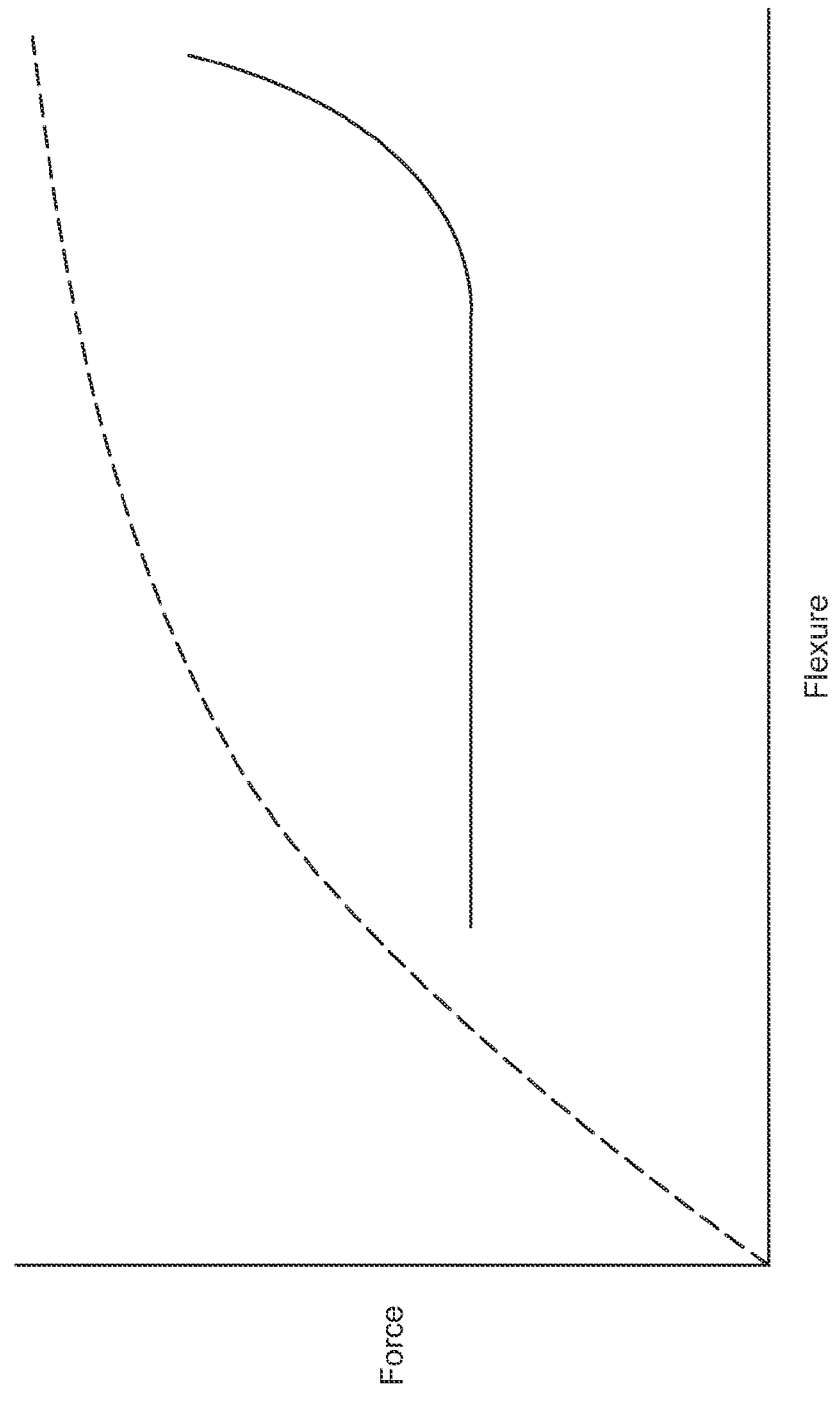
FIG. 6 shows a graph plotting resistive force as a function of flexure for the implant shown in FIG. 4A and for a conventional implant.

FIG. 6 shows a graph depicting the expected resistive forces as a function of flexure for a conventional implant (plotted as a dashed line) versus the implant disclosed in the present application (plotted as a solid line). As shown in the graph of FIG. 6, as a conventional implant flexes, the implant resists flexing along a linear path so that the resistive force increases as the flexure increases. At a particular degree of flexure, past the elastic limit and within the plastic limit of the material, the resistive force offered by a conventional implant peaks with a permanent deformation.

In contrast, as shown in FIG. 6, the flexure force of the implant disclosed in the present application is relatively constant to flex during the early stages of flexure or strain and becomes more difficult to flex during the latter stages of flexure. As a result, the implant of the present invention will provide little resistance for a sustained flexure of the implant, and significantly greater levels of resistance will not occur until significant flexure of the implant occurs.

As shown in the graph in FIG. 6, during a significant portion of bending the implant 20, the implant is relatively easy to bend, yet provide adequate support to the soft tissues of the tongue to prevent collapse. During more pronounced flexing and bending, however, the implant 20 becomes more resistive to further flexing.

Although the present invention is not limited by any particular theory of operation, it is believed that using implants having one or more compressible chambers enables a sustained elastic response to effectively provide a relatively constant flexure force through a larger displacement. This maintains a constant force on the surrounding tissues so that the wakeful motions of the soft tissues do not experience an increase in applied force, which makes the implants less noticeable when awake. In one embodiment, the compressible chambers desirably accommodate fluid deformation without increasing the geometry of the part in the axis associated with the compressible fluid compartments.

Figure 7A:
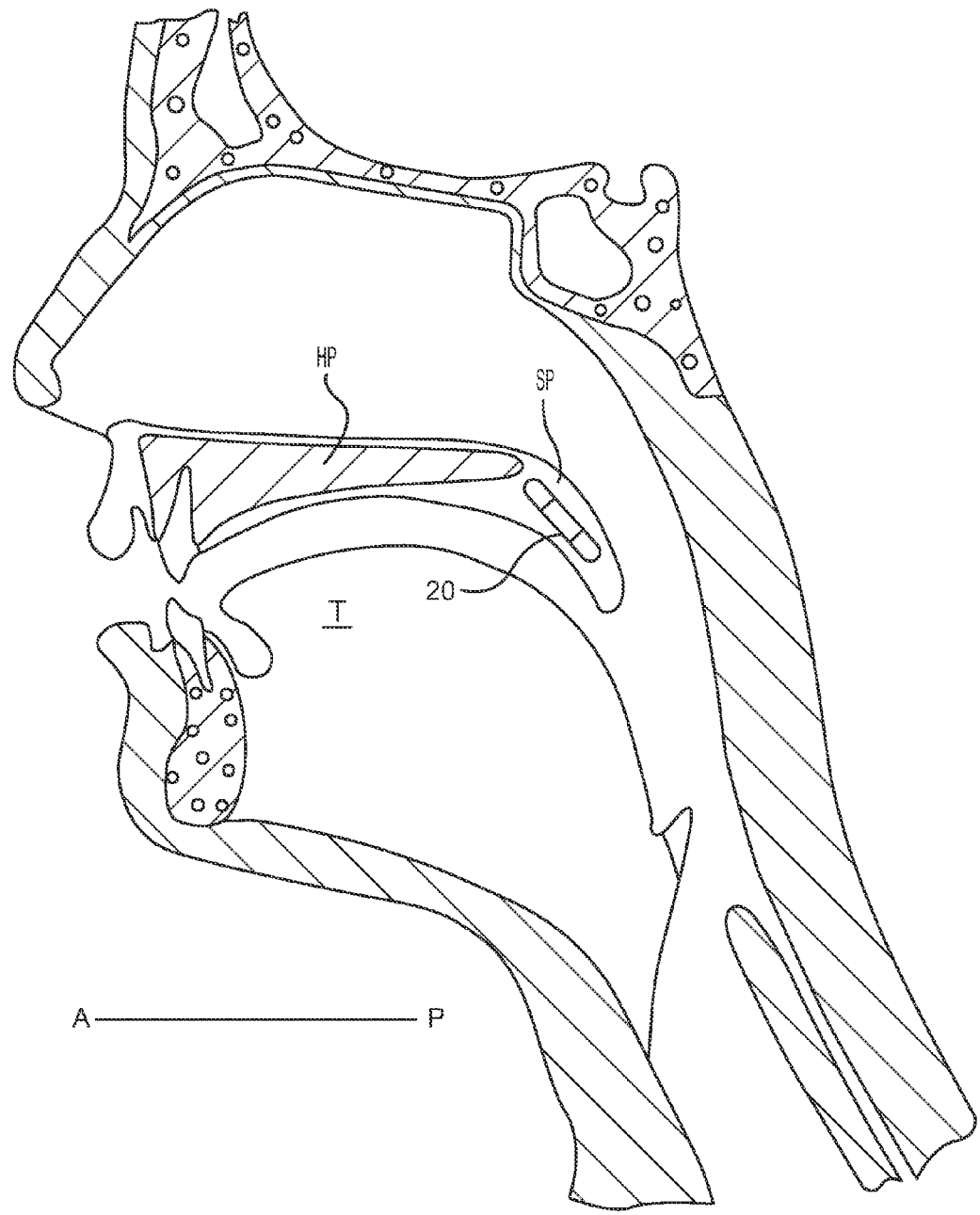
FIG. 7A shows the implant of FIG. 4A implanted in a soft palate, in accordance with one embodiment of the present invention.
Figure 7B:
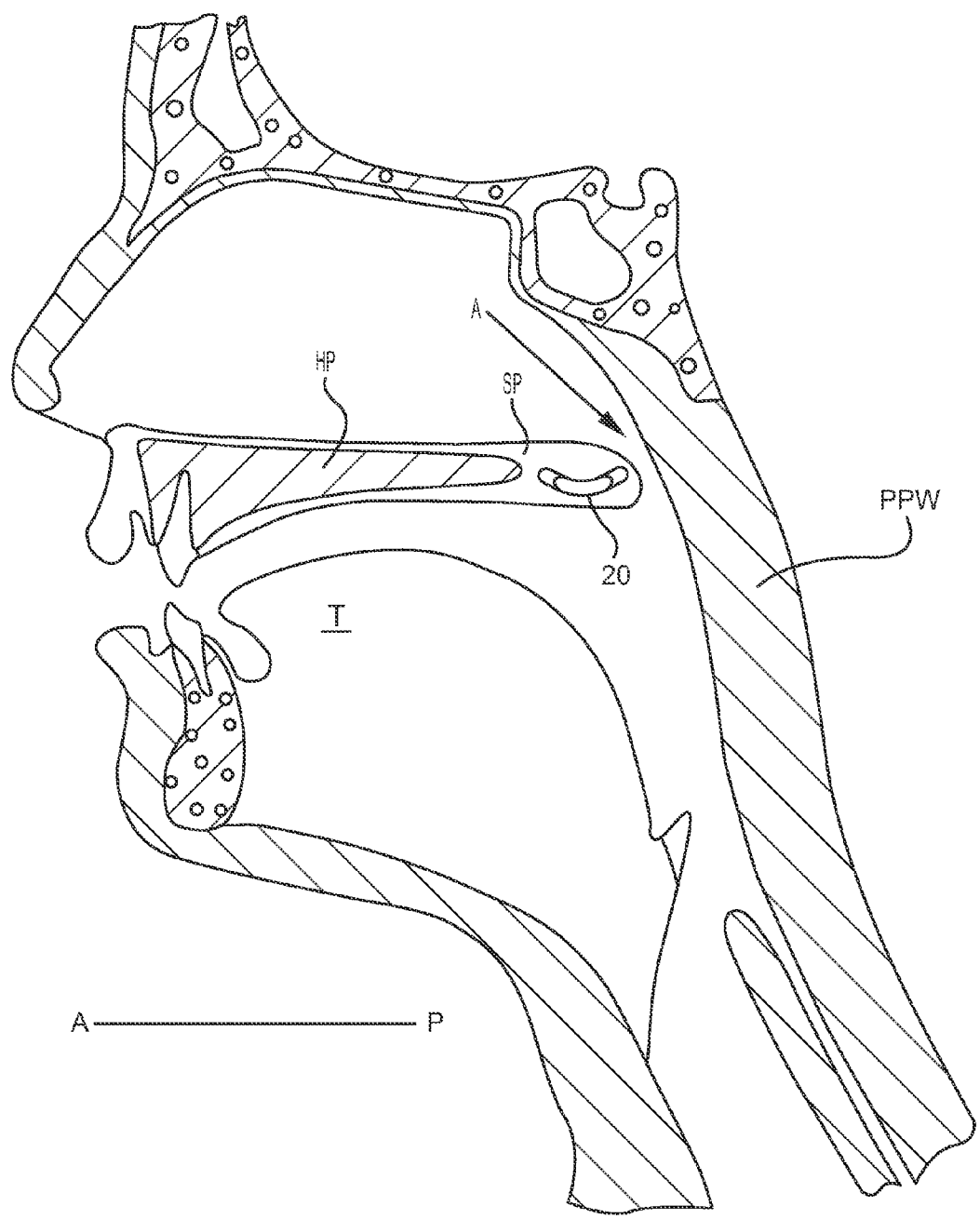
FIG. 7B shows the implant of FIG. 7A during flexing of the implant.

Referring to FIG. 7A, in one embodiment, a flexible implant 20 as described herein may be implanted within a soft palate SP of a patient. In the particular embodiment shown in FIG. 7A, a single flexible fluid filled implant 20 is implanted within the soft palate SP tissue that is posterior to the hard palate HP of a patient. When the patient is awake, the soft palate SP retains its shape and form as shown in FIG. 7A. During sleep, however, the soft palate SP may relax which causes the posterior end of the soft palate SP to move closer to the opposing posterior pharyngeal wall PPW, as shown in FIG. 7B. If the posterior end of the soft palate SP moves close enough to the opposing posterior pharyngeal wall PPW, the upper airway A may be at least partially blocked or closed for causing an episode of obstructive sleep apnea. Although the present invention is not limited by any particular theory of operation, it is believed that implanting an implant disclosed herein within the soft palate SP will prevent closing of the airway A because the implant will resist further movement of the posterior end of the soft palate SP toward the opposing pharyngeal wall PPW. As shown in FIG. 7B, as the soft palate relaxes, the flexible implant 20 flexes and bends relative to the longitudinal axis thereof. As the implant 20 flexes and bends, the incompressible fluid within the central chamber forces the first and second flexible diaphragms to extend into the outer chambers for compressing the compressible fluid within the outer chambers, which increases the pressure level of the fluid within the outer chambers slightly maintaining the flexural force of the implant 20 without an increase in external dimensions of the implant. The reduced flexibility of the implant 20, in turn, resists further movement of the soft palate SP toward the opposing posterior pharyngeal wall PPW. Upon completion of muscular contractions applying loading to the implant, the incompressible fluid returns compartment to it's original geometry providing support to the tongue in the relaxed condition.

Figure 8:
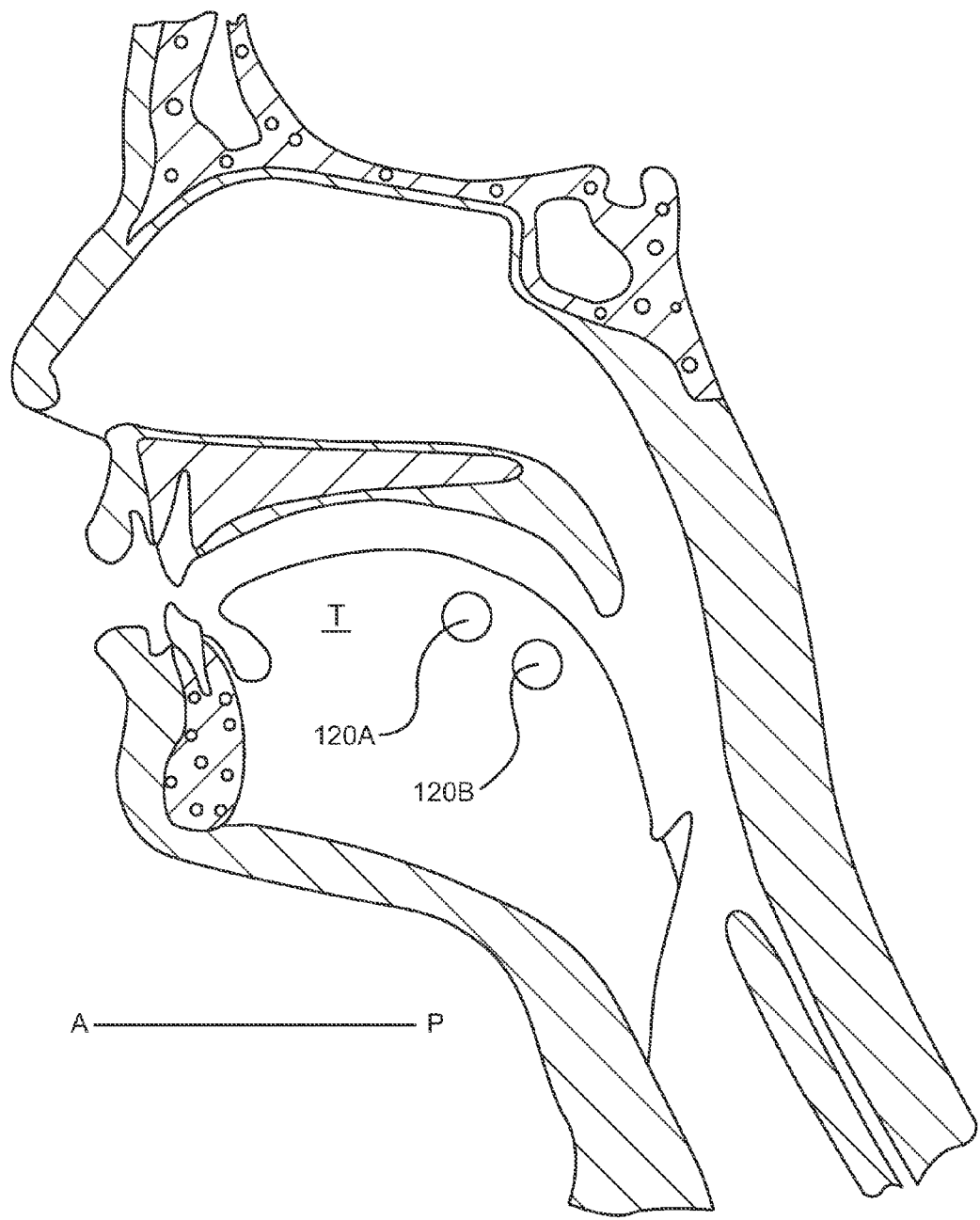
FIG. 8 shows a system for treating obstructive sleep apnea including a pair of flexible implants that are implanted in a tongue in a transverse direction, in accordance with one embodiment of the present invention.

Referring to FIG. 8, in one embodiment, two flexible implants 120A, 120B are implanted in the base of a tongue T. Each of the flexible implants 120A, 120B desirably has a longitudinal axis that extends in a lateral direction relative to the anterior-posterior axis of the patient. Although the embodiment shown in FIG. 8 is not limited by any particular theory of operation, it is believed that implanting one or more laterally extending flexible implants may support the sides of the tongue T. This implantation configuration may be useful treating OSA episodes resulting from one or more sides of the tongue collapsing toward one or more lateral pharyngeal walls of a patient.

Figure 9:
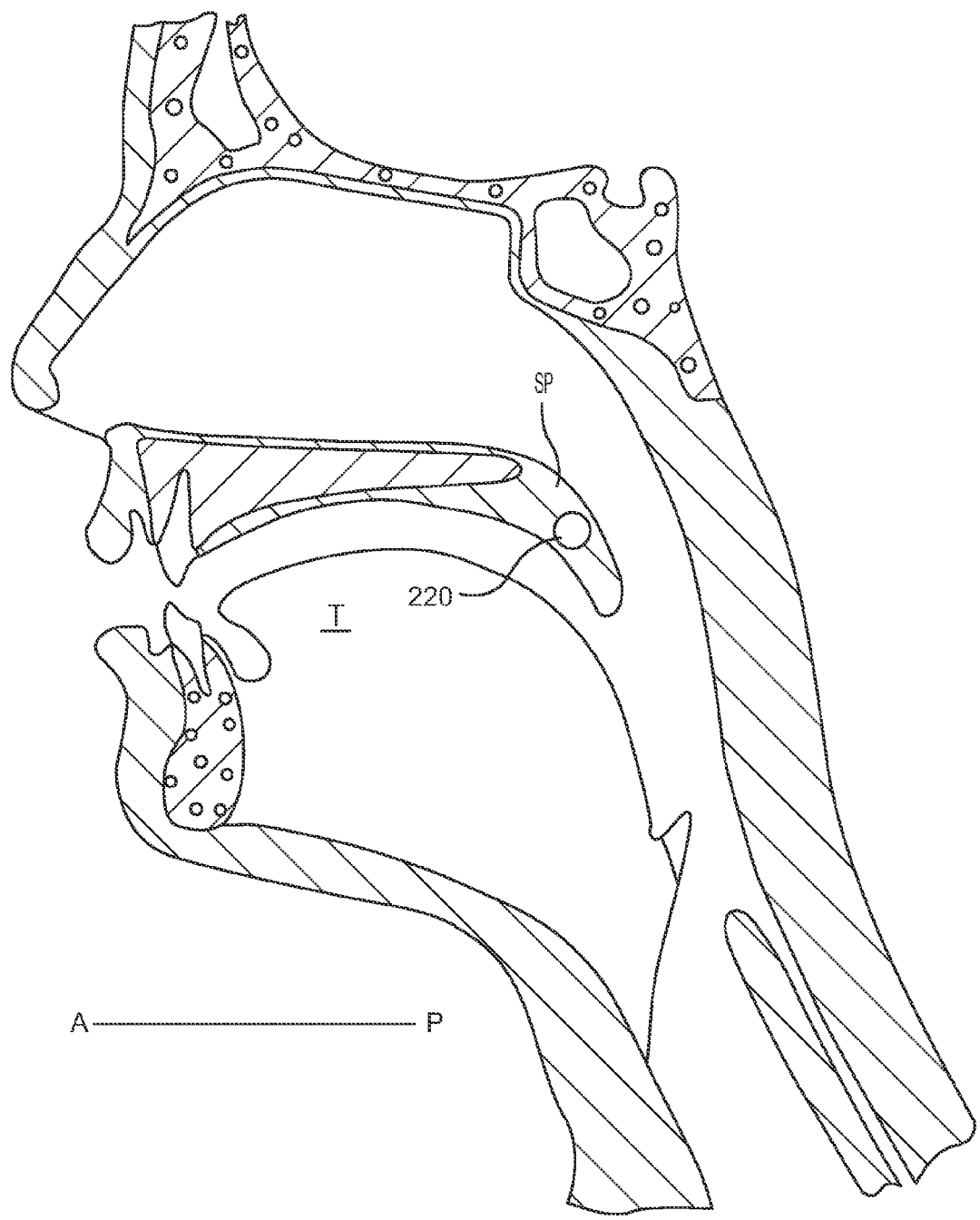
FIG. 9 shows a system for treating obstructive sleep apnea including a flexible implant that is implanted in a soft palate in a transverse direction, in accordance with one embodiment of the present invention.

Referring to FIG. 9, in one embodiment, a system for treating obstructive sleep apnea includes a fluid filled implant 220 that is implantable within the soft palate SP of a patient. The implanted flexible fluid filled implant 220 desirably extends a lateral direction that is substantially perpendicular to the anterior-posterior axis of the patient. The laterally extending implant 220 desirably prevents the one or more lateral ends of the soft palate from collapsing against an opposing lateral pharyngeal wall. Although only one implant 220 is shown in FIG. 9, other embodiments may be include two or more transversely extending flexible implants implantable in the soft palate SP.

Figure 10:
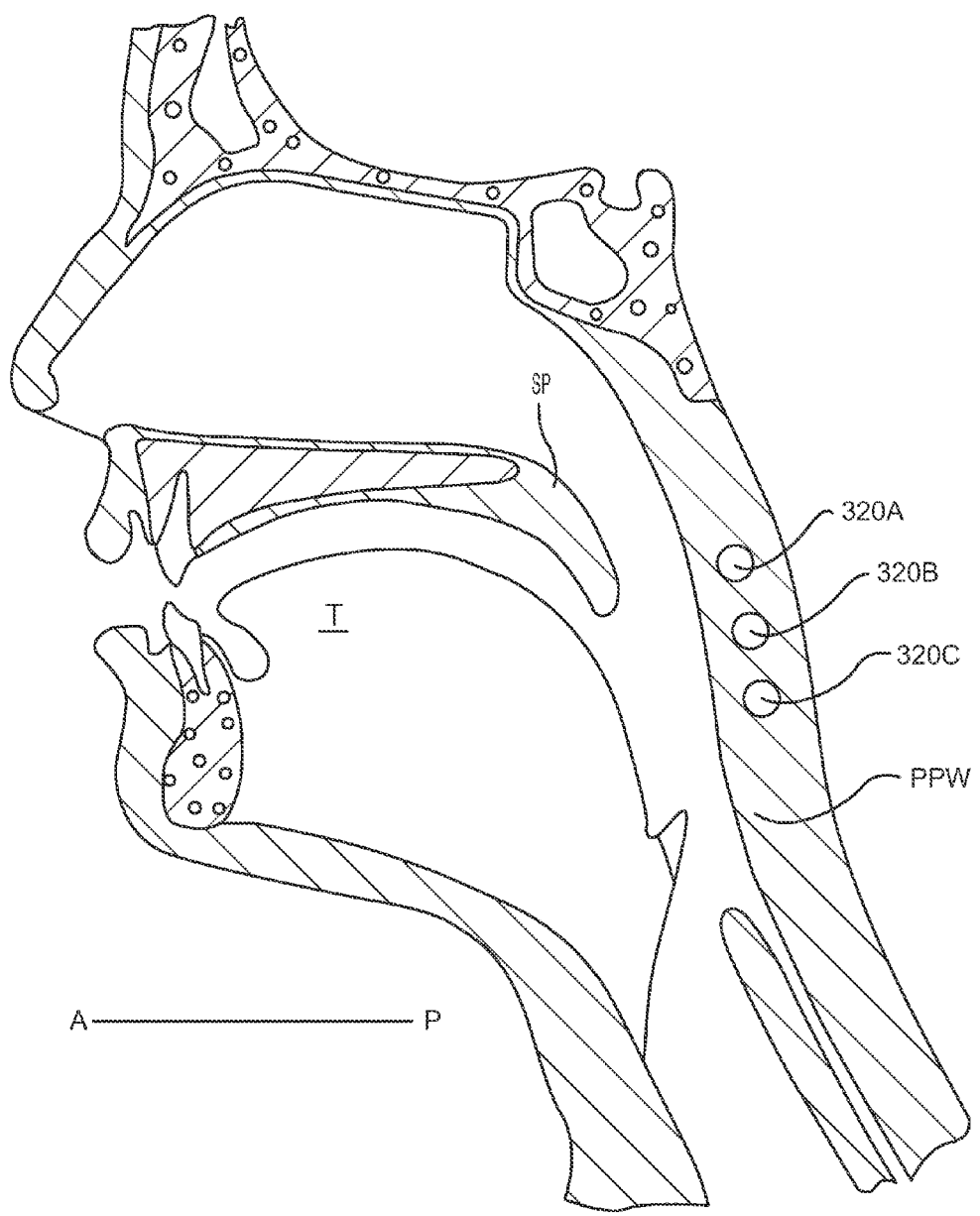
FIG. 10 shows a system for treating obstructive sleep apnea including implants that are implanted in a posterior pharyngeal wall in a transverse direction, in accordance with one embodiment of the present invention.

Referring to FIG. 10, in one embodiment, a system for treating obstructive sleep apnea includes a set of flexible implants 320A, 320B, 320C that are implanted in a patients' posterior pharyngeal wall PPW. The respective implants 320A-320C have longitudinal axes that preferably extend in transverse directions relative to the anterior-posterior axis of the patient. In one embodiment, the flexible implants 320A-320C prevent the posterior pharyngeal wall from collapsing inwardly toward the base of the tongue and/or the soft palate SP. The flexible fluid filled implants 320A-320C may also be implanted within one or more of the lateral pharyngeal walls. Although three implants are shown in FIG. 10, in other embodiments fewer or more implants may be used. In certain embodiments, only one or two of the implants shown in FIG. 10 may be implanted in the pharyngeal wall.

Figure 11:
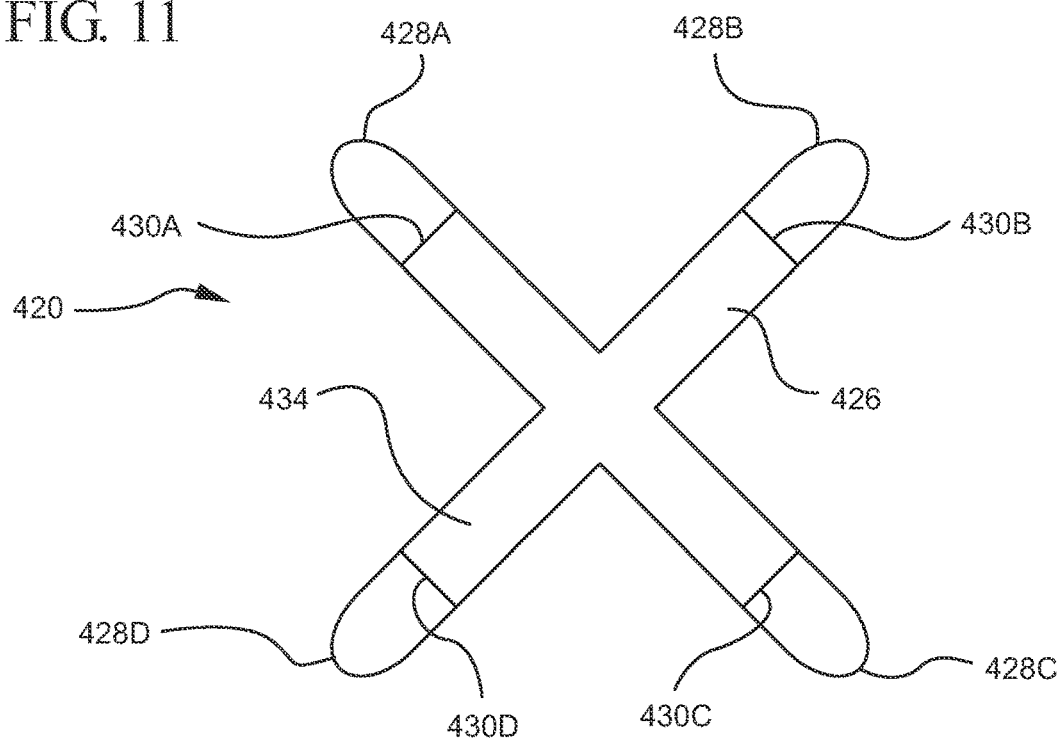
FIG. 11 shows an implant for treating obstructive sleep apnea, in accordance with one embodiment of the present invention.

Referring to FIG. 11, in one embodiment, a system for treating obstructive sleep apnea includes a flexible fluid filled implant 420 having a central chamber 426 filled with an incompressible fluid and outer chambers 428A-428D that are filled with compressible fluids. The flexible fluid filled implant 420 has an X-shaped configuration. The central chamber 426 is filled with incompressible fluid such as water, saline, or flowable gel. A first flexible diaphragm 430A separates the central chamber 426 from a first outer chamber 428A; a second flexible diaphragm 430B separates the central chamber 426 from a second outer chamber 428B; a third flexible diaphragm 430C separates the central chamber 426 from a third outer chamber 428C; and a fourth flexible diaphragm 430D separates the central chamber 426 from a fourth outer chamber 428D. As described above, as the implant 420 flexes or bends due to external forces (e.g. a relaxed tongue), the incompressible fluid 434 within the central chamber 426 forces the four flexible diaphragms 430A-430D to move outwardly into the outer chambers 428A-428D containing the compressible fluid. In response, the compressible fluid 436 within the outer chambers 428A-428D is compressed, slightly increasing the pressure within the outer chambers only slightly reducing the flexibility of the implant 420, thereby maintaining the resistance to further flexing movement.

Figure 12:
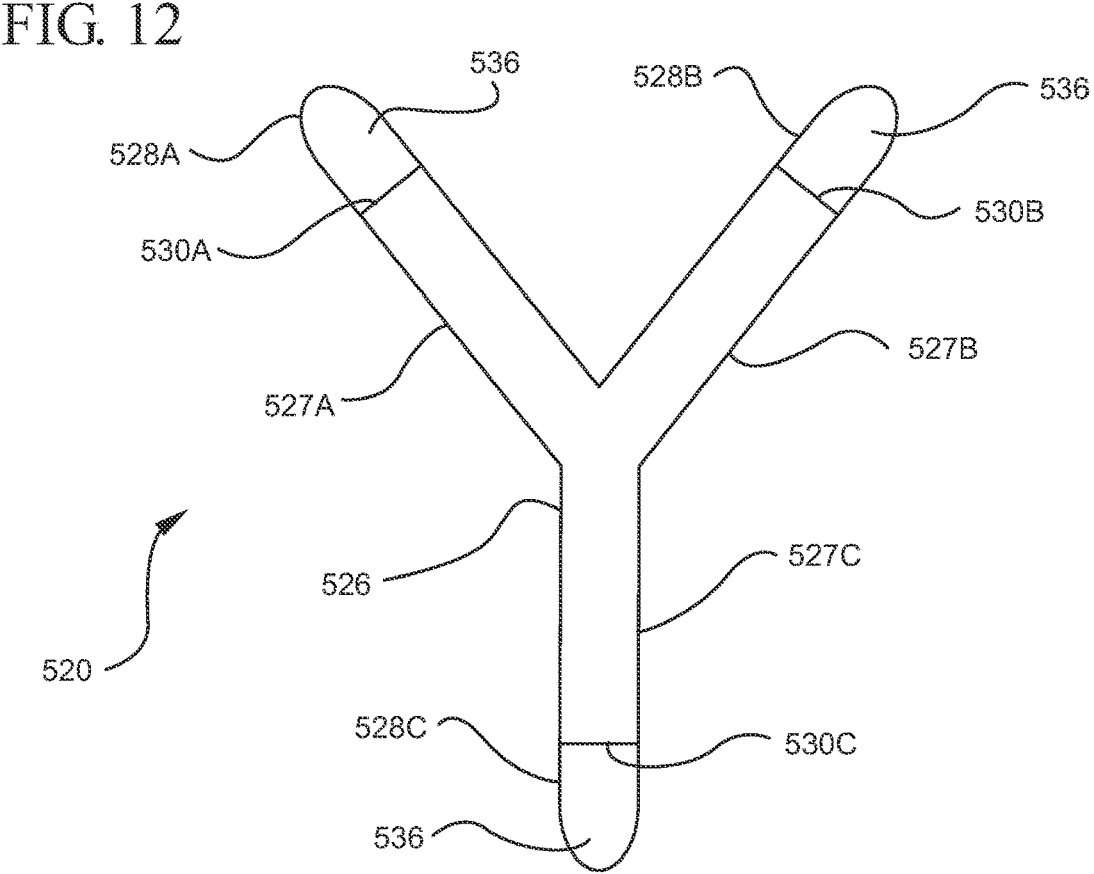
FIG. 12 shows an implant for treating obstructive sleep apnea, in accordance with another embodiment of the present invention.

Referring to FIG. 12, in one embodiment, a flexible fluid filled implant 520 has a Y-shaped configuration. The implant 520 includes a central chamber 526 defining a first leg 527A, a second leg 527B and a third leg 527C. The central chamber 526 is desirably filled with an incompressible fluid such as saline, water, or flowable gel. The flexible fluid filled implant 520 desirably includes outer chambers 528A-528C that are desirable separated from the central chamber 526 via flexible diaphragms 530A-530C. The outer chambers 528A-528C are desirably filled with a compressible fluid such as air or nitrogen. As the flexible implant 520 flexes due to external forces, the incompressible fluid 534 within the central chamber 528 forces the flexible diaphragms 432A-432C to move outwardly into the outer chambers 528A-528C so as to reduce the volume of the compressible fluid 536 within the outer chambers 528A-528C. As the volume within the outer chambers 528A-1528C is reduced, the compressible fluid within the outer chambers is compressed. During a significant portion of flexing, the compressible fluid 536 provides little or no increase in resistance to further flexing. The rigidity of the implant only appreciably increases after significant flexing.

Figure 13A:
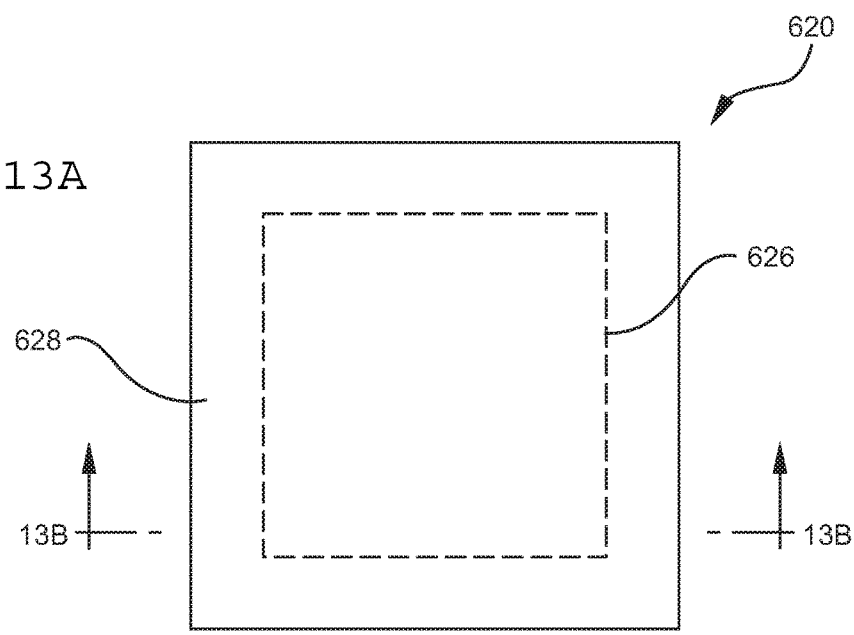
FIG. 13A shows a top plan view of an implant for treating obstructive sleep apnea, in accordance with one embodiment of the present invention.
Figure 13B:
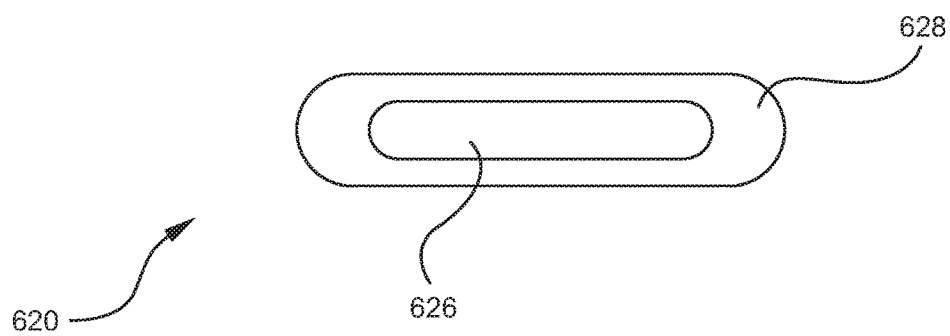
FIG. 13B shows a cross-sectional view of the implant shown in FIG. 13A.

Referring to FIG. 13A, in one embodiment, a flexible implant 620 includes a central chamber 626 and an outer chamber 628 that surrounds the central chamber 626. The central chamber 626 is filled with an incompressible fluid 634 and the outer chamber 628 is preferably filled with a compressible fluid 636. As the flexible implant 620 flexes, the physical distortion of the central chamber 626 reduces the volume within the outer chamber 628 so as to compress the compressible fluid 636 within the outer chamber 628. During a significant portion of flexing, the compressible fluid 636 provides little or no increase in resistance to further flexing. The rigidity of the implant only appreciably increases during significant flexing, due to significant compression of the compressible fluid within the outer chamber 628.

Figure 14:
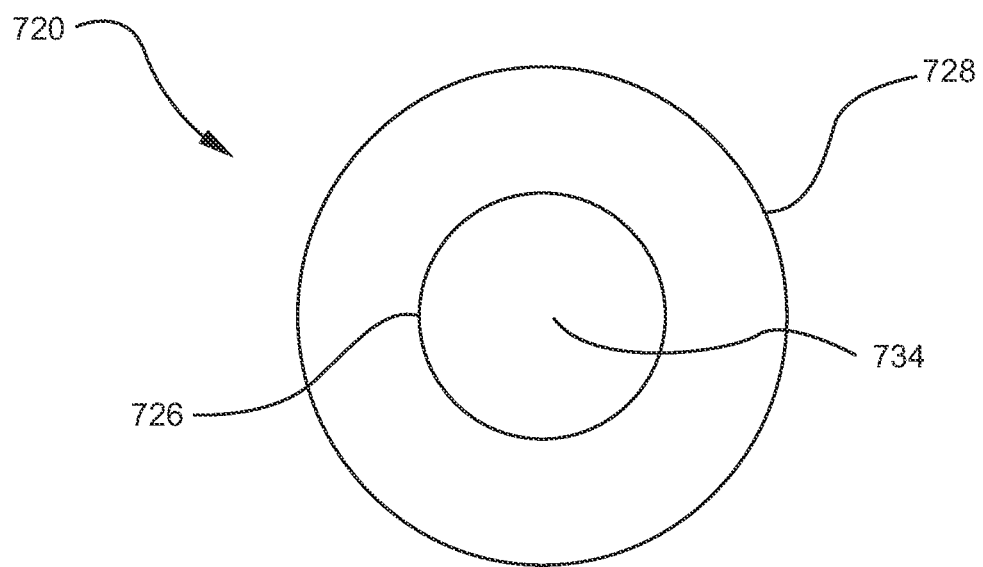
FIG. 14 shows a cross-sectional view of an implant for treating obstructive sleep apnea, in accordance with another embodiment of the present invention.

Referring to FIG. 14, in one embodiment, a flexible implant 720 preferably has a spherical shape. The flexible fluid filled implant 720 includes a central chamber 726 and an outer chamber 728 that surrounds the central chamber 726. The central chamber 726 is desirably filled with an incompressible fluid 734. The outer chamber 728 is desirably filled with a compressible fluid 736. During flexing of the implant 720, the central chamber 726 is physically distorted which reduces the volume of the outer chamber 728. As the volume of the outer chamber 728 is reduced, the compressible fluid 736 within the outer chamber 728 is compressed so as to eventually reduce the flexibility of the implant 720.

Figure 15:
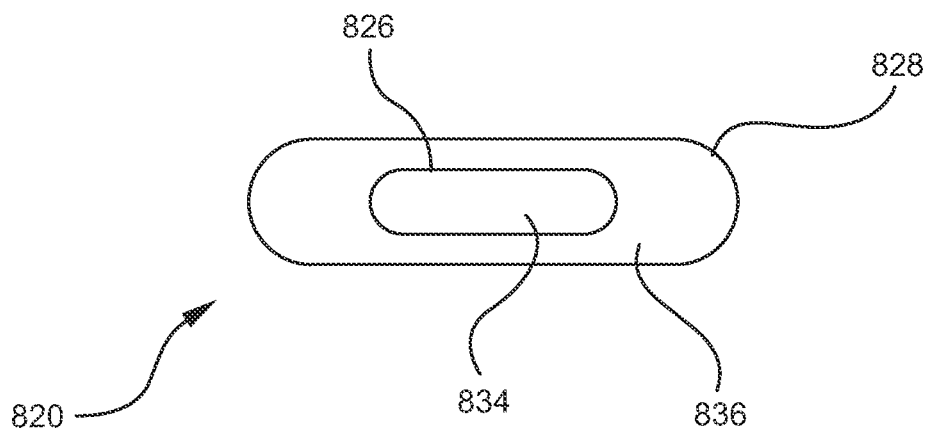
FIG. 15 shows a cross-sectional view of an implant for treating obstructive sleep apnea in accordance with one embodiment of the present invention.

Referring to FIG. 15, in one embodiment, a flexible implant 820 has a composite construction including a first chamber 826 and a second chamber 828 that surrounds the first chamber 826. Thus, the first chamber 826 is disposed within the second chamber 828. In one embodiment, the first chamber 826 is filled with an incompressible fluid 834 and the second chamber 828 is preferably filled with a compressible fluid 836. As external forces are applied to the flexible implant 820, the physical distortion of the first chamber 826 reduces the volume within the second chamber 828 so as to compress the compressible fluid 836 within the second chamber 828. During a significant portion of flexing, the compressible fluid 836 provides little or no increase in resistance to further flexing. The rigidity of the implant only appreciably increases during significant flexing, due to significant compression of the compressible fluid within the second chamber 828. In an alternate embodiment, the first chamber 826 may be filled with a compressible fluid and the second chamber 828 may be filed with an incompressible fluid.

The present invention provides a number of advantages over prior art methods and devices used for treating obstructive sleep apnea syndrome and hypopnea. First, the methods, systems and devices disclosed herein provide for simple surgical procedures that are minimally invasive. Typically, the methods, systems and devices disclosed herein may be utilized during an outpatient procedure. In addition, the methods, systems and devices disclosed herein provide both immediate and long term results for treating obstructive sleep apnea syndrome and hypopnea. Moreover, the methods, systems and devices disclosed herein do not require a significant level of patient compliance.

Additionally, the devices disclosed provide adequate support to the soft tissues of the airway and do not impart significant forces on the soft tissues during wakeful muscular activities such as speaking or swallowing. Flexure of the device does not cause an increase in dimensions of the implant thereby minimizing the compression of abutting tissues or unwanted dissection of tissue planes.

In addition, the present invention does not anchor the tongue to a fixed hard structure, such as the mandible. Thus, the present invention is significantly less likely to affect swallowing or speech, thereby providing a great improvement over prior art methods, systems and devices. The present invention also preferably uses materials having long-term biocompatibility.

Although various embodiments disclosed herein relate to use in humans, it is contemplated that the present invention may be used in all mammals, and in all animals having air passages. Moreover, the methods, systems and devices disclosed herein may incorporate any materials that are biocompatible, as well as any solutions or components that minimize rejection, enhance tissue ingrowth, enhance the formation of mucosal layers, and improve acceptance of the device by a body after the device has been implanted.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof. As such, the scope of the present invention is to be limited only as set forth in the appended claims.

What is claimed is:

1. An implant for treating obstructive sleep apnea comprising:
    a first sealed chamber containing an incompressible fluid, wherein said first sealed chamber has no passages for introducing said incompressible fluid into said first sealed chamber or removing said incompressible fluid from said first sealed chamber;

a second sealed chamber surrounding said first sealed chamber and containing a compressible fluid, wherein said first and second sealed chambers are completely sealed, and wherein said second sealed chamber has no passages for introducing said compressible fluid into said second sealed chamber or removing said compressible fluid from said second sealed chamber, wherein said second sealed chamber surrounds said first sealed chamber so that said first sealed chamber is entirely disposed within said second sealed chamber; and a flexible diaphragm separating said incompressible fluid within said first sealed chamber from said compressible fluid within said second sealed chamber, wherein said second sealed chamber defines an outer perimeter of said implant, and wherein said flexible diaphragm is spaced from the outer perimeter of said implant on all sides of said flexible diaphragm so that said compressible fluid contained within said second sealed chamber completely surrounds all of the sides of said flexible diaphragm.

2. The implant as claimed in claim 1, wherein said first sealed chamber has a first volume that is adapted to remain constant during flexing of said implant and said second sealed chamber has a second volume that is adapted to change during flexing of said implant, and wherein flexing of said implant does not increase the dimensions of said implant.

3. The implant as claimed in claim 2, wherein during flexing of said implant said first sealed chamber is adapted to physically distort and said incompressible fluid within said first sealed chamber is adapted to force said flexible diaphragm to extend into said second sealed chamber for reducing the second volume of said second sealed chamber and compressing said compressible fluid in said second sealed chamber.

4. The implant as claimed in claim 1, wherein application of an external force upon said first sealed chamber is adapted to distort said first sealed chamber whereupon said incompressible fluid within said first sealed chamber is adapted to force said flexible diaphragm to extend into said second sealed chamber for compressing said compressible fluid within said second sealed chamber without increasing the dimensions of said implant.

5. The implant as claimed in claim 1, wherein said implant comprises biocompatible polymeric materials or biocompatible elastomeric materials.

6. The implant as claimed in claim 1, wherein said incompressible fluid within said first sealed chamber is selected from the group consisting of liquids, water, saline solution and flowable gels.

7. The implant as claimed in claim 1, wherein said compressible fluid within said second sealed chamber is selected from the group consisting of gasses, air, and nitrogen.

8. The implant as claimed in claim 1, wherein said implant has a longitudinal axis that is capable of being aligned with an anterior-posterior, transverse, vertical, or horizontal axis of a patient, or a longitudinal axis that is capable of being angled relative to the anterior-posterior, transverse, vertical, or horizontal axis of the patient.

9. The implant as claimed in claim 1, wherein said implant is implantable within soft tissue of an oropharyngeal airway.

10. The implant as claimed in claim 1, wherein said implant is implantable within a tongue, a soft palate, or a pharyngeal wall.

11. An implant for treating obstructive sleep apnea having internal volume shifting capabilities comprising:

a first chamber containing an incompressible fluid;

a second chamber surrounding said first chamber, said second chamber containing a compressible fluid, wherein said second chamber completely surrounds said first chamber so that said first chamber is entirely disposed within said second chamber;

a flexible diaphragm separating said incompressible fluid in said first chamber from said compressible fluid in said second chamber, wherein said first chamber has no valves for introducing said incompressible fluid into said first chamber or removing said incompressible fluid from said first chamber and said second chamber has no valves for introducing said compressible fluid into said second chamber or removing said compressible fluid from said second chamber, wherein said second chamber defines an outer perimeter of said implant, and wherein said flexible diaphragm is spaced from the outer perimeter of said implant on all sides of said flexible diaphragm so that said compressible fluid contained within said second chamber completely surrounds all of the sides of said flexible diaphragm.

12. The implant as claimed in claim 11, wherein first chamber has a first volume that is adapted to remain constant during the application of the external force upon said implant and said second chamber has a second volume that is adapted to change during the application of the external force upon said implant.

13. The implant as claimed in claim 11, wherein said implant comprises biocompatible polymeric materials or biocompatible elastomeric materials.

14. The implant as claimed in claim 11, wherein said incompressible fluid in said first chamber is selected from the group consisting of liquids, water, saline solution and flowable gels, and said compressible fluid in said second chamber is selected from the group consisting of gasses, air, and nitrogen.

15. The implant as claimed in claim 11, wherein said implant has a longitudinal axis that is alignable with an anterior-posterior, transverse, vertical, or horizontal axis of a patient, or a longitudinal axis that is angled relative to the anterior-posterior, transverse, vertical, or horizontal axis of the patient.

16. The implant as claimed in claim 11, wherein said implant is implantable within soft tissue of an oropharyngeal airway.

17. The implant as claimed in claim 11, wherein said implant is implantable within a tongue, a soft palate, or a pharyngeal wall.

18. A flexible implant used for treating obstructive sleep apnea having internal volume shifting capabilities comprising:

a central chamber containing an incompressible fluid;

an outer chamber completely surrounding said central chamber so that said central chamber is entirely disposed within said outer chamber, said outer chamber containing a compressible fluid;

a flexible diaphragm separating said incompressible fluid in said central chamber from said compressible fluid in said outer chamber, wherein said central chamber has no valves for introducing said incompressible fluid into said central chamber or removing said incompressible fluid from said central chamber and said outer chamber has no valves for introducing said compressible fluid into said outer chamber or removing said compressible fluid from said outer chamber, wherein flexing said implant is capable of physically distorting said central chamber so that said incompressible fluid in said central chamber shifts internally within said implant to force said flexible diaphragm to extend into said outer chamber to compress said compressible fluid in said outer chamber, wherein said outer chamber defines an outer perimeter of said flexible implant, wherein said flexible diaphragm is spaced from the outer perimeter of said flexible implant on all sides of said flexible diaphragm so that said compressible fluid in said outer chamber completely surrounds all of the sides of said flexible diaphragm.

19. The implant as claimed in claim 18, wherein central chamber has a first volume that is capable of remaining constant during flexure of said implant and said outer chamber has a second volume that is capable of changing during the flexure of said implant without changing the dimensions of said implant.

20. The implant as claimed in claim 18, wherein said flexible diaphragm is capable of extending into said outer chamber for reducing the volume of said outer chamber and compressing said first compressible fluid within said outer chamber.

21. The implant as claimed in claim 18, wherein said incompressible fluid in said central chamber is selected from the group consisting of liquids, water, saline and flowable gels, and said compressible fluid in said outer chamber is selected from the group consisting of gasses, air, and nitrogen.

* * * * *